(12) United States Patent
Bays et al.

(10) Patent No.: US 10,512,470 B1
(45) Date of Patent: Dec. 24, 2019

(54) OSTEOTOMY PROCEDURE FOR CORRECTING BONE MISALIGNMENT

(71) Applicant: Treace Medical Concepts, Inc., Ponte Vedra Beach, FL (US)

(72) Inventors: F. Barry Bays, Collierville, TN (US); Joe W. Ferguson, Ponte Vedra Beach, FL (US); Carlos Eduardo Gil, Jacksonville, FL (US); Tyler Hissong, Jacksonville, FL (US); Danielle Peterson, Jacksonville, FL (US); Sean F. Scanlan, Jacksonville, FL (US); Michael Stedham, Jacksonville, FL (US); Justin Valentine, St. Augustine, FL (US)

(73) Assignee: Treace Medical Concepts, Inc., Ponte Vedra, FL (US)

( * ) Notice: Subject to any disclaimer, the term of this patent is extended or adjusted under 35 U.S.C. 154(b) by 166 days.

(21) Appl. No.: 15/687,986

(22) Filed: Aug. 28, 2017

Related U.S. Application Data

(60) Provisional application No. 62/380,074, filed on Aug. 26, 2016.

(51) Int. Cl.
 *A61B 17/15* (2006.01)
(52) U.S. Cl.
 CPC ............ *A61B 17/151* (2013.01); *A61B 17/15* (2013.01)
(58) Field of Classification Search
 CPC .............................. A61B 17/15; A61B 17/151
 USPC .................................................. 606/86 R, 87
 See application file for complete search history.

(56) References Cited

U.S. PATENT DOCUMENTS

| | | | |
|---|---|---|---|
| 2,557,364 | A | 6/1951 | Tillson |
| 3,159,952 | A | 12/1964 | Lipkins |
| 4,069,824 | A | 1/1978 | Weinstock |
| 4,159,716 | A | 7/1979 | Borchers |
| 4,187,840 | A | 2/1980 | Watanabe |
| 4,335,715 | A | 6/1982 | Kirkley |
| 4,338,927 | A | 7/1982 | Volkov et al. |

(Continued)

FOREIGN PATENT DOCUMENTS

| | | |
|---|---|---|
| AU | 2009227957 B2 | 7/2014 |
| CA | 2491824 A1 | 9/2005 |

(Continued)

OTHER PUBLICATIONS

Albano et al., "Biomechanical Study of Transcortical or Transtrabecular Bone Fixation of Patellar Tendon Graft wih Bioabsorbable Pins in ACL Reconstruction in Sheep," Revista Brasileira de Ortopedia (Rev Bras Ortop.) vol. 47, No. 1, 2012, pp. 43-49.

(Continued)

*Primary Examiner* — Eric S Gibson
(74) *Attorney, Agent, or Firm* — Fredrikson & Byron, P.A.

(57) ABSTRACT

An osteotomy procedure may be performed to correct a misalignment of a bone, such as a bunion deformity. In some examples, the osteotomy procedure involves making a first crescentic-shaped cut transecting a first metatarsal, thereby forming a concave-shaped end and a convex-shaped end on opposed bone portions. The method further involves making a second crescentic-shaped cut across the concave-shaped end of one bone portion and thereafter moving the bone portions relative to each other in multiple planes to correct an anatomical misalignment.

36 Claims, 25 Drawing Sheets

(56) References Cited

U.S. PATENT DOCUMENTS

| | | | |
|---|---|---|---|
| 4,349,018 A | 9/1982 | Chambers | |
| 4,409,973 A * | 10/1983 | Neufeld | A61B 17/1637 606/178 |
| 4,440,168 A | 4/1984 | Warren | |
| 4,501,268 A | 2/1985 | Comparetto | |
| 4,502,474 A | 3/1985 | Comparetto | |
| 4,509,511 A * | 4/1985 | Neufeld | A61B 17/15 606/82 |
| 4,565,191 A | 1/1986 | Slocum | |
| 4,570,624 A | 2/1986 | Wu | |
| 4,627,425 A | 12/1986 | Reese | |
| 4,628,919 A | 12/1986 | Clybum | |
| 4,632,102 A | 12/1986 | Comparetto | |
| 4,664,102 A | 5/1987 | Comparetto | |
| 4,677,973 A * | 7/1987 | Slocum | A61B 17/1637 606/60 |
| 4,708,133 A | 11/1987 | Comparetto | |
| 4,750,481 A | 6/1988 | Reese | |
| 4,757,810 A | 7/1988 | Reese | |
| 4,787,908 A | 11/1988 | Wyss et al. | |
| 4,895,141 A | 1/1990 | Koeneman et al. | |
| 4,952,214 A | 8/1990 | Comparetto | |
| 4,978,347 A | 12/1990 | Ilizarov | |
| 4,988,349 A | 1/1991 | Pennig | |
| 4,995,875 A | 2/1991 | Coes | |
| 5,021,056 A | 6/1991 | Hofmann et al. | |
| 5,035,698 A | 7/1991 | Comparetto | |
| 5,042,983 A | 8/1991 | Rayhack | |
| 5,049,149 A | 9/1991 | Schmidt | |
| 5,053,039 A | 10/1991 | Hofmann et al. | |
| 5,078,719 A | 1/1992 | Schreiber | |
| 5,112,334 A | 5/1992 | Alchermes et al. | |
| 5,147,364 A | 9/1992 | Comparetto | |
| 5,176,685 A | 1/1993 | Rayhack | |
| 5,207,676 A | 5/1993 | Canadell et al. | |
| 5,246,444 A | 9/1993 | Schreiber | |
| 5,254,119 A | 10/1993 | Schreiber | |
| 5,312,412 A | 5/1994 | Whipple | |
| 5,358,504 A | 10/1994 | Paley et al. | |
| 5,364,402 A | 11/1994 | Mumme et al. | |
| 5,413,579 A | 5/1995 | Tom Du Toit | |
| 5,417,694 A | 5/1995 | Marik et al. | |
| 5,449,360 A | 9/1995 | Schreiber | |
| 5,470,335 A | 11/1995 | Du Toit | |
| 5,490,854 A | 2/1996 | Fisher et al. | |
| 5,529,075 A | 6/1996 | Clark | |
| 5,540,695 A | 7/1996 | Levy | |
| 5,578,038 A | 11/1996 | Slocum | |
| 5,601,565 A | 2/1997 | Huebner | |
| 5,613,969 A | 3/1997 | Jenkins, Jr. | |
| 5,620,442 A | 4/1997 | Bailey et al. | |
| 5,620,448 A | 4/1997 | Puddu | |
| 5,643,270 A | 7/1997 | Combs | |
| 5,667,510 A | 9/1997 | Combs | |
| H1706 H | 1/1998 | Mason | |
| 5,722,978 A | 3/1998 | Jenkins | |
| 5,749,875 A | 5/1998 | Puddu | |
| 5,765,648 A | 6/1998 | Sheehan et al. | |
| 5,779,709 A | 7/1998 | Harris et al. | |
| 5,788,695 A | 8/1998 | Richardson | |
| 5,803,924 A | 9/1998 | Oni et al. | |
| 5,810,822 A | 9/1998 | Mortier | |
| 5,843,085 A * | 12/1998 | Graser | A61B 17/15 606/87 |
| 5,893,553 A | 4/1999 | Pinkous | |
| 5,911,724 A | 6/1999 | Wehrli | |
| 5,928,234 A * | 7/1999 | Manspeizer | A61B 17/6425 606/54 |
| 5,935,128 A | 8/1999 | Carter et al. | |
| 5,941,877 A | 8/1999 | Viegas et al. | |
| 5,951,556 A | 9/1999 | Faccioli et al. | |
| 5,980,526 A | 11/1999 | Johnson et al. | |
| 5,984,931 A | 11/1999 | Greenfield | |
| 6,007,535 A | 12/1999 | Rayhack et al. | |
| 6,027,504 A | 2/2000 | McGuire | |
| 6,030,391 A * | 2/2000 | Brainard | A61B 17/15 606/82 |
| 6,162,223 A | 12/2000 | Orsak et al. | |
| 6,171,309 B1 | 1/2001 | Huebner | |
| 6,203,545 B1 | 3/2001 | Stoffella | |
| 6,248,109 B1 | 6/2001 | Stoffella | |
| 6,391,031 B1 * | 5/2002 | Toomey | A61B 17/15 606/82 |
| 6,478,799 B1 | 11/2002 | Williamson | |
| 6,511,481 B2 | 1/2003 | Von Hoffmann et al. | |
| 6,547,793 B1 | 4/2003 | McGuire | |
| 6,676,662 B1 | 1/2004 | Bagga et al. | |
| 6,719,773 B1 | 4/2004 | Boucher et al. | |
| 6,743,233 B1 | 6/2004 | Baldwin et al. | |
| 6,755,838 B2 | 6/2004 | Trnka | |
| 6,796,986 B2 | 9/2004 | Duffner | |
| 6,859,661 B2 | 2/2005 | Tuke | |
| 7,018,383 B2 | 3/2006 | McGuire | |
| 7,033,361 B2 | 4/2006 | Collazo | |
| 7,112,204 B2 | 9/2006 | Justin et al. | |
| 7,182,766 B1 | 2/2007 | Mogul | |
| 7,241,298 B2 | 7/2007 | Nemec et al. | |
| 7,282,054 B2 | 10/2007 | Steffensmeier et al. | |
| 7,377,924 B2 | 5/2008 | Raistrick et al. | |
| 7,465,303 B2 | 12/2008 | Riccione et al. | |
| 7,540,874 B2 | 6/2009 | Trumble et al. | |
| 7,572,258 B2 | 8/2009 | Stiernborg | |
| 7,641,660 B2 | 1/2010 | Lakin et al. | |
| D610,257 S | 2/2010 | Horton | |
| 7,686,811 B2 | 3/2010 | Byrd et al. | |
| 7,691,108 B2 | 4/2010 | Lavallee | |
| 7,763,026 B2 | 7/2010 | Egger et al. | |
| D629,900 S | 12/2010 | Fisher | |
| 7,967,823 B2 | 6/2011 | Ammann et al. | |
| 7,972,338 B2 | 7/2011 | O'Brien | |
| D646,389 S | 10/2011 | Claypool et al. | |
| 8,057,478 B2 | 11/2011 | Kuczynski et al. | |
| 8,062,301 B2 | 11/2011 | Ammann et al. | |
| D651,315 S | 12/2011 | Bertoni et al. | |
| D651,316 S | 12/2011 | May et al. | |
| 8,080,010 B2 | 12/2011 | Schulz et al. | |
| 8,083,746 B2 | 12/2011 | Novak | |
| 8,123,753 B2 | 2/2012 | Poncet | |
| 8,137,406 B2 | 3/2012 | Novak et al. | |
| 8,147,530 B2 | 4/2012 | Strnad et al. | |
| 8,167,918 B2 | 5/2012 | Strnad et al. | |
| 8,172,848 B2 | 5/2012 | Tomko et al. | |
| 8,192,441 B2 | 6/2012 | Collazo | |
| 8,197,487 B2 | 6/2012 | Poncet et al. | |
| 8,231,623 B1 | 7/2012 | Jordan | |
| 8,231,663 B2 | 7/2012 | Kay et al. | |
| 8,236,000 B2 | 8/2012 | Ammann et al. | |
| 8,246,561 B1 | 8/2012 | Agee et al. | |
| D666,721 S | 9/2012 | Wright et al. | |
| 8,262,664 B2 | 9/2012 | Justin et al. | |
| 8,277,459 B2 | 10/2012 | Sand et al. | |
| 8,282,644 B2 | 10/2012 | Edwards | |
| 8,282,645 B2 * | 10/2012 | Lawrence | A61B 17/15 606/87 |
| 8,292,966 B2 | 10/2012 | Morton | |
| 8,303,596 B2 | 11/2012 | Plassky et al. | |
| 8,313,492 B2 | 11/2012 | Wong et al. | |
| 8,323,289 B2 | 12/2012 | Re | |
| 8,337,503 B2 | 12/2012 | Lian | |
| 8,343,159 B2 | 1/2013 | Bennett | |
| 8,377,105 B2 | 2/2013 | Bscher | |
| D679,395 S | 4/2013 | Wright et al. | |
| 8,409,209 B2 | 4/2013 | Ammann et al. | |
| 8,435,246 B2 | 5/2013 | Fisher et al. | |
| 8,475,462 B2 | 7/2013 | Thomas et al. | |
| 8,496,662 B2 | 7/2013 | Novak et al. | |
| 8,518,045 B2 | 8/2013 | Szanto | |
| 8,523,870 B2 | 9/2013 | Green, II et al. | |
| 8,529,571 B2 | 9/2013 | Horan et al. | |
| 8,535,317 B2 | 9/2013 | Szanto | |
| 8,540,777 B2 | 9/2013 | Ammann et al. | |
| D694,884 S | 12/2013 | Mooradian et al. | |
| D695,402 S | 12/2013 | Dacosta et al. | |

(56) References Cited

U.S. PATENT DOCUMENTS

| | | |
|---|---|---|
| 8,652,142 B2 | 2/2014 | Geissler |
| 8,657,820 B2 | 2/2014 | Kubiak et al. |
| D701,303 S | 3/2014 | Cook |
| 8,672,945 B2 | 3/2014 | Lavallee et al. |
| 8,696,716 B2 | 4/2014 | Kartalian et al. |
| 8,702,715 B2 | 4/2014 | Ammann et al. |
| D705,929 S | 5/2014 | Frey |
| 8,715,363 B2 | 5/2014 | Ratron et al. |
| 8,728,084 B2 | 5/2014 | Berelsman et al. |
| 8,758,354 B2 | 6/2014 | Habegger et al. |
| 8,764,760 B2 | 7/2014 | Metzger et al. |
| 8,764,763 B2 | 7/2014 | Wong et al. |
| 8,771,279 B2 | 7/2014 | Philippon et al. |
| 8,777,948 B2 | 7/2014 | Bernsteiner |
| 8,784,427 B2 | 7/2014 | Fallin et al. |
| 8,784,457 B2 | 7/2014 | Graham |
| 8,795,286 B2 | 8/2014 | Sand et al. |
| 8,801,727 B2 | 8/2014 | Chan et al. |
| 8,808,303 B2 | 8/2014 | Stemniski et al. |
| 8,828,012 B2 | 9/2014 | May et al. |
| 8,858,602 B2 * | 10/2014 | Weiner ................ A61B 17/151 606/282 |
| 8,882,778 B2 | 11/2014 | Ranft |
| 8,882,816 B2 | 11/2014 | Kartalian et al. |
| 8,888,785 B2 | 11/2014 | Ammann et al. |
| D720,456 S | 12/2014 | Dacosta et al. |
| 8,900,247 B2 | 12/2014 | Tseng et al. |
| 8,906,026 B2 | 12/2014 | Ammann et al. |
| 8,915,922 B2 | 12/2014 | Szanto et al. |
| 8,945,132 B2 | 2/2015 | Plassky et al. |
| 8,998,903 B2 | 4/2015 | Price et al. |
| 8,998,904 B2 | 4/2015 | Zeetser et al. |
| D730,132 S | 5/2015 | Szanto |
| 9,023,052 B2 | 5/2015 | Lietz et al. |
| 9,044,250 B2 | 6/2015 | Olsen et al. |
| 9,060,822 B2 | 6/2015 | Lewis et al. |
| 9,089,376 B2 | 7/2015 | Medoff et al. |
| 9,101,421 B2 | 8/2015 | Blacklidge |
| 9,107,715 B2 | 8/2015 | Blitz et al. |
| 9,113,920 B2 | 8/2015 | Ammann et al. |
| D740,424 S | 10/2015 | Dacosta et al. |
| 9,427,240 B2 * | 8/2016 | Von Zabern ......... A61B 17/151 |
| D765,844 S | 9/2016 | DaCosta |
| D766,434 S | 9/2016 | DaCosta |
| D766,437 S | 9/2016 | DaCosta |
| D766,438 S | 9/2016 | DaCosta |
| D766,439 S | 9/2016 | DaCosta |
| 9,545,276 B2 * | 1/2017 | Buchanan ........... A61B 17/8061 |
| 9,750,538 B2 | 9/2017 | Soffiatti et al. |
| 9,750,551 B1 | 9/2017 | Nichols |
| 9,785,747 B2 | 10/2017 | Geebelen |
| 10,028,750 B2 | 7/2018 | Rose |
| 10,064,631 B2 | 9/2018 | Dacosta et al. |
| 10,159,499 B2 | 12/2018 | Dacosta et al. |
| 10,292,713 B2 | 5/2019 | Fallin et al. |
| 10,327,829 B2 | 6/2019 | Dacosta et al. |
| 2002/0099381 A1 | 7/2002 | Maroney |
| 2002/0107519 A1 | 8/2002 | Dixon et al. |
| 2002/0165552 A1 | 11/2002 | Duffner |
| 2002/0198531 A1 | 12/2002 | Millard et al. |
| 2004/0010259 A1 | 1/2004 | Keller et al. |
| 2004/0039394 A1 | 2/2004 | Conti et al. |
| 2004/0065117 A1 | 4/2004 | Chen et al. |
| 2004/0097946 A1 | 5/2004 | Dietzel et al. |
| 2004/0138669 A1 | 7/2004 | Horn |
| 2005/0004676 A1 | 1/2005 | Schon et al. |
| 2005/0059978 A1 | 3/2005 | Sherry et al. |
| 2005/0070909 A1 | 3/2005 | Egger et al. |
| 2005/0075641 A1 | 4/2005 | Singhatat et al. |
| 2005/0101961 A1 | 5/2005 | Huebner et al. |
| 2005/0149042 A1 | 7/2005 | Metzger |
| 2005/0228389 A1 | 10/2005 | Stiernborg |
| 2005/0251147 A1 | 11/2005 | Novak |
| 2005/0273112 A1 | 12/2005 | McNamara |
| 2006/0015102 A1 * | 1/2006 | Toullec .............. A61B 17/8061 606/86 B |
| 2006/0129163 A1 | 6/2006 | McGuire |
| 2006/0206044 A1 | 9/2006 | Simon |
| 2006/0217733 A1 | 9/2006 | Plassky et al. |
| 2006/0229621 A1 | 10/2006 | Cadmus |
| 2006/0241607 A1 | 10/2006 | Myerson et al. |
| 2006/0241608 A1 * | 10/2006 | Myerson ............ A61B 17/8061 606/280 |
| 2006/0264961 A1 | 11/2006 | Murray-Brown |
| 2007/0010818 A1 | 1/2007 | Stone et al. |
| 2007/0123857 A1 | 5/2007 | Deffenbaugh et al. |
| 2007/0233138 A1 | 10/2007 | Figueroa et al. |
| 2007/0265634 A1 | 11/2007 | Weinstein |
| 2007/0276383 A1 | 11/2007 | Rayhack |
| 2008/0009863 A1 | 1/2008 | Bond et al. |
| 2008/0039850 A1 | 2/2008 | Rowley et al. |
| 2008/0091197 A1 | 4/2008 | Coughlin |
| 2008/0140081 A1 | 6/2008 | Heavener et al. |
| 2008/0147073 A1 | 6/2008 | Ammann et al. |
| 2008/0172054 A1 | 7/2008 | Claypool et al. |
| 2008/0195215 A1 | 8/2008 | Morton |
| 2008/0208252 A1 | 8/2008 | Holmes |
| 2008/0262500 A1 | 10/2008 | Collazo |
| 2008/0269908 A1 | 10/2008 | Warburton |
| 2009/0036893 A1 | 2/2009 | Kartalian et al. |
| 2009/0036931 A1 | 2/2009 | Pech et al. |
| 2009/0054899 A1 | 2/2009 | Ammann et al. |
| 2009/0093849 A1 | 4/2009 | Grabowski |
| 2009/0105767 A1 | 4/2009 | Reiley |
| 2009/0118733 A1 | 5/2009 | Orsak et al. |
| 2009/0198244 A1 | 8/2009 | Leibel |
| 2009/0198279 A1 | 8/2009 | Zhang et al. |
| 2009/0222047 A1 | 9/2009 | Graham |
| 2009/0254092 A1 | 10/2009 | Albiol Llorach |
| 2009/0254126 A1 | 10/2009 | Orbay et al. |
| 2009/0287309 A1 | 11/2009 | Walch et al. |
| 2010/0069910 A1 | 3/2010 | Hasselman |
| 2010/0121334 A1 | 5/2010 | Couture et al. |
| 2010/0130981 A1 | 5/2010 | Richards |
| 2010/0152782 A1 | 6/2010 | Stone et al. |
| 2010/0168799 A1 | 7/2010 | Schumer |
| 2010/0185245 A1 | 7/2010 | Paul et al. |
| 2010/0249779 A1 | 9/2010 | Hotchkiss et al. |
| 2010/0256687 A1 | 10/2010 | Neufeld et al. |
| 2010/0274293 A1 * | 10/2010 | Terrill ................ A61B 17/8057 606/286 |
| 2010/0318088 A1 | 12/2010 | Warne et al. |
| 2010/0324556 A1 | 12/2010 | Tyber et al. |
| 2011/0093084 A1 | 4/2011 | Morton |
| 2011/0245835 A1 | 10/2011 | Dodds et al. |
| 2011/0288550 A1 | 11/2011 | Orbay et al. |
| 2011/0301648 A1 | 12/2011 | Lofthouse et al. |
| 2012/0016426 A1 | 1/2012 | Robinson |
| 2012/0065689 A1 | 3/2012 | Prasad et al. |
| 2012/0078258 A1 | 3/2012 | Lo et al. |
| 2012/0123420 A1 | 5/2012 | Honiball |
| 2012/0123484 A1 | 5/2012 | Lietz et al. |
| 2012/0130376 A1 | 5/2012 | Loring et al. |
| 2012/0130383 A1 | 5/2012 | Budoff |
| 2012/0184961 A1 | 7/2012 | Johannaber |
| 2012/0185056 A1 | 7/2012 | Warburton |
| 2012/0191199 A1 | 7/2012 | Raemisch |
| 2012/0239045 A1 | 9/2012 | Li |
| 2012/0253350 A1 | 10/2012 | Anthony et al. |
| 2012/0265301 A1 | 10/2012 | Demers et al. |
| 2012/0277745 A1 | 11/2012 | Lizee et al. |
| 2012/0330135 A1 | 12/2012 | Millahn et al. |
| 2013/0012949 A1 | 1/2013 | Fallin et al. |
| 2013/0035694 A1 | 2/2013 | Grimm et al. |
| 2013/0085499 A1 | 4/2013 | Lian |
| 2013/0096563 A1 | 4/2013 | Meade et al. |
| 2013/0131821 A1 | 5/2013 | Cachia |
| 2013/0150903 A1 | 6/2013 | Vincent |
| 2013/0158556 A1 | 6/2013 | Jones et al. |
| 2013/0165936 A1 | 6/2013 | Myers |
| 2013/0165938 A1 | 6/2013 | Chow et al. |
| 2013/0172942 A1 | 7/2013 | Lewis et al. |
| 2013/0184714 A1 | 7/2013 | Kaneyama et al. |

(56) References Cited

U.S. PATENT DOCUMENTS

| | | |
|---|---|---|
| 2013/0190765 A1 | 7/2013 | Harris et al. |
| 2013/0190766 A1 | 7/2013 | Harris et al. |
| 2013/0204259 A1 | 8/2013 | Zajac |
| 2013/0226248 A1 | 8/2013 | Hatch et al. |
| 2013/0226252 A1 | 8/2013 | Mayer |
| 2013/0231668 A1 | 9/2013 | Olsen et al. |
| 2013/0237987 A1 | 9/2013 | Graham |
| 2013/0237989 A1 | 9/2013 | Bonutti |
| 2013/0267956 A1 | 10/2013 | Terrill et al. |
| 2013/0310836 A1 | 11/2013 | Raub et al. |
| 2013/0325019 A1 | 12/2013 | Thomas et al. |
| 2013/0325076 A1 | 12/2013 | Palmer et al. |
| 2013/0331845 A1 | 12/2013 | Horan et al. |
| 2013/0338785 A1 | 12/2013 | Wong |
| 2014/0005672 A1 | 1/2014 | Edwards et al. |
| 2014/0025127 A1 | 1/2014 | Richter |
| 2014/0039501 A1 | 2/2014 | Schickendantz et al. |
| 2014/0039561 A1 | 2/2014 | Weiner et al. |
| 2014/0046387 A1 | 2/2014 | Waizenegger |
| 2014/0074099 A1 | 3/2014 | Vigneron et al. |
| 2014/0074101 A1 | 3/2014 | Collazo |
| 2014/0094861 A1 | 4/2014 | Fallin |
| 2014/0094924 A1 | 4/2014 | Hacking et al. |
| 2014/0135775 A1 | 5/2014 | Maxson et al. |
| 2014/0163563 A1 | 6/2014 | Reynolds et al. |
| 2014/0171953 A1 | 6/2014 | Gonzalvez et al. |
| 2014/0180342 A1 | 6/2014 | Lowery et al. |
| 2014/0188139 A1* | 7/2014 | Fallin ............... A61B 17/0491 606/145 |
| 2014/0194884 A1 | 7/2014 | Martin et al. |
| 2014/0194999 A1 | 7/2014 | Orbay et al. |
| 2014/0207144 A1 | 7/2014 | Lee et al. |
| 2014/0249537 A1 | 9/2014 | Wong et al. |
| 2014/0257308 A1 | 9/2014 | Johannaber |
| 2014/0257509 A1 | 9/2014 | Dacosta et al. |
| 2014/0276815 A1 | 9/2014 | Riccione |
| 2014/0276853 A1 | 9/2014 | Long et al. |
| 2014/0277176 A1* | 9/2014 | Buchanan ........... A61B 17/8061 606/281 |
| 2014/0277214 A1 | 9/2014 | Helenbolt et al. |
| 2014/0288562 A1* | 9/2014 | Von Zabern ......... A61B 17/151 606/88 |
| 2014/0296995 A1 | 10/2014 | Reiley et al. |
| 2014/0303621 A1 | 10/2014 | Gerold et al. |
| 2014/0336658 A1 | 11/2014 | Luna et al. |
| 2014/0343555 A1 | 11/2014 | Russi et al. |
| 2015/0032168 A1 | 1/2015 | Orsak et al. |
| 2015/0045801 A1 | 2/2015 | Axelson, Jr. et al. |
| 2015/0045839 A1 | 2/2015 | Dacosta et al. |
| 2015/0051650 A1 | 2/2015 | Verstreken et al. |
| 2015/0057667 A1 | 2/2015 | Ammann et al. |
| 2015/0066094 A1 | 3/2015 | Prandi et al. |
| 2015/0112446 A1 | 4/2015 | Melamed et al. |
| 2015/0119944 A1 | 4/2015 | Geldwert |
| 2015/0142064 A1 | 5/2015 | Perez et al. |
| 2015/0150608 A1 | 6/2015 | Sammarco |
| 2015/0182273 A1 | 7/2015 | Stemniski et al. |
| 2015/0223851 A1 | 8/2015 | Hill et al. |
| 2015/0245858 A1 | 9/2015 | Weiner et al. |
| 2016/0015426 A1 | 1/2016 | Dayton et al. |
| 2016/0022315 A1 | 1/2016 | Soffiatti et al. |
| 2016/0151165 A1 | 6/2016 | Fallin et al. |
| 2016/0175089 A1 | 6/2016 | Fallin et al. |
| 2016/0192950 A1 | 7/2016 | Dayton et al. |
| 2016/0192970 A1 | 7/2016 | Dayton et al. |
| 2016/0199076 A1 | 7/2016 | Fallin et al. |
| 2016/0213384 A1 | 7/2016 | Fallin et al. |
| 2016/0235414 A1 | 8/2016 | Hatch et al. |
| 2016/0242791 A1 | 8/2016 | Fallin et al. |
| 2016/0256204 A1 | 9/2016 | Patel et al. |
| 2016/0324532 A1 | 11/2016 | Montoya et al. |
| 2016/0354127 A1 | 12/2016 | Lundquist et al. |
| 2017/0014173 A1* | 1/2017 | Smith ............... A61B 17/1728 |
| 2017/0042598 A1* | 2/2017 | Santrock ........... A61B 17/8866 |
| 2017/0042599 A1* | 2/2017 | Bays ............... A61B 17/8866 |
| 2017/0079669 A1* | 3/2017 | Bays ............... A61B 17/15 |
| 2017/0143511 A1 | 5/2017 | Cachia |
| 2017/0164989 A1 | 6/2017 | Weiner et al. |
| 2018/0110530 A1* | 4/2018 | Wagner ............ A61B 17/8866 |
| 2018/0344334 A1 | 12/2018 | Kim et al. |

FOREIGN PATENT DOCUMENTS

| | | |
|---|---|---|
| CA | 2854997 A1 | 5/2013 |
| CH | 695846 A5 | 9/2006 |
| CN | 1457968 A | 11/2003 |
| CN | 2930668 Y | 8/2007 |
| CN | 201558162 U | 8/2010 |
| CN | 201572172 U | 9/2010 |
| CN | 201586060 U | 9/2010 |
| CN | 201912210 U | 8/2011 |
| CN | 101237835 B | 11/2012 |
| CN | 202801773 U | 3/2013 |
| CN | 103462675 A | 12/2013 |
| CN | 103505276 A | 1/2014 |
| CN | 203458450 U | 3/2014 |
| CN | 102860860 B | 5/2014 |
| CN | 203576647 U | 5/2014 |
| CN | 104490460 A | 4/2015 |
| CN | 104510523 A | 4/2015 |
| CN | 104523327 A | 4/2015 |
| CN | 104546102 A | 4/2015 |
| CN | 204379413 U | 6/2015 |
| CN | 204410951 U | 6/2015 |
| CN | 204428143 U | 7/2015 |
| CN | 204428144 U | 7/2015 |
| CN | 204428145 U | 7/2015 |
| CN | 204446081 U | 7/2015 |
| DE | 2255312 A1 | 5/1974 |
| DE | 4425456 A1 | 3/1996 |
| DE | 202006010241 U1 | 3/2007 |
| DE | 102007053058 B3 | 4/2009 |
| EP | 685206 B1 | 9/2000 |
| EP | 1508316 B1 | 5/2007 |
| EP | 1897509 B1 | 7/2009 |
| EP | 2124772 A1 | 12/2009 |
| EP | 2124832 B1 | 8/2012 |
| EP | 2632349 A1 | 9/2013 |
| EP | 2665428 A1 | 11/2013 |
| EP | 2742878 A1 | 6/2014 |
| EP | 2750617 A1 | 7/2014 |
| EP | 2849684 A1 | 3/2015 |
| EP | 2624764 B1 | 12/2015 |
| FR | 2304322 A1 | 10/1976 |
| FR | 2362616 A1 | 3/1978 |
| FR | 2764183 B1 | 11/1999 |
| FR | 2953120 B1 | 1/2012 |
| FR | 3030221 A1 | 6/2016 |
| GB | 2154143 A | 9/1985 |
| GB | 2154144 A | 9/1985 |
| GB | 2334214 B | 1/2003 |
| IN | 200903719 P1 | 6/2009 |
| IN | 200904479 P2 | 5/2010 |
| IN | 140/DELNP/2012 P1 | 2/2013 |
| IN | 2004/KOLNP/2013 P2 | 11/2013 |
| JP | 4134243 B2 | 8/2008 |
| JP | 4162380 B2 | 10/2008 |
| JP | 2011092405 A | 5/2011 |
| JP | 2011523889 A | 8/2011 |
| JP | 4796943 B2 | 10/2011 |
| JP | 5466647 B2 | 4/2014 |
| JP | 2014511207 A | 5/2014 |
| JP | 2014521384 A | 8/2014 |
| JP | 5628875 B2 | 11/2014 |
| KR | 100904142 B1 | 6/2009 |
| RU | 2074810 C1 | 3/1997 |
| RU | 2098036 C1 | 12/1997 |
| RU | 2195892 C2 | 1/2003 |
| RU | 2320287 C1 | 3/2008 |
| RU | 2321366 C2 | 4/2008 |
| RU | 2321369 C1 | 4/2008 |
| RU | 2346663 C2 | 2/2009 |
| RU | 2412662 C1 | 2/2011 |
| SU | 1333328 A2 | 8/1987 |

(56) References Cited

FOREIGN PATENT DOCUMENTS

| | | |
|---|---|---|
| WO | 0166022 A1 | 9/2001 |
| WO | 03075775 A1 | 9/2003 |
| WO | 2004089227 A2 | 10/2004 |
| WO | 2008051064 A1 | 5/2008 |
| WO | 2009029798 A1 | 3/2009 |
| WO | 2009032101 A2 | 3/2009 |
| WO | 2011037885 A1 | 3/2011 |
| WO | 2012029008 A1 | 3/2012 |
| WO | 2013090392 A1 | 6/2013 |
| WO | 2013134387 A1 | 9/2013 |
| WO | 2013169475 A1 | 11/2013 |
| WO | 2014020561 A1 | 2/2014 |
| WO | 2014022055 A1 | 2/2014 |
| WO | 2014035991 A1 | 3/2014 |
| WO | 2014085882 A1 | 6/2014 |
| WO | 2014147099 A1 | 9/2014 |
| WO | 2014152219 A2 | 9/2014 |
| WO | 2014152535 A1 | 9/2014 |
| WO | 2014177783 A1 | 11/2014 |
| WO | 2014200017 A1 | 12/2014 |
| WO | 2015094409 A1 | 6/2015 |
| WO | 2015105880 A1 | 7/2015 |
| WO | 2015127515 A2 | 9/2015 |
| WO | 2016134160 A1 | 8/2016 |

OTHER PUBLICATIONS

Anderson et al., "Uncemented STAR Total Ankle Prostheses," The Journal of Bone and Joint Surgery, vol. 86(1, Suppl 2), Sep. 2004, pp. 103-111, (Abstract Only).

Dayton et al., "Is Our Current Paradigm for Evaluation and Management of the Bunion Deformity Flawed? A Discussion of Procedure Philosophy Relative to Anatomy," The Journal of Foot and Ankle Surgery, vol. 54, 2015, pp. 102-111.

Dayton et al., "Observed Changes in Radiographic Measurements of the First Ray after Frontal and Transverse Plane Rotation of the Hallux: Does the Hallux Drive the Metatarsal in a Bunion Deformity?," The Journal of Foot and Ankle Surgery, vol. 53, 2014, pp. 584-587.

Dayton et al., "Relationship of Frontal Plane Rotation of First Metatarsal to Proximal Articular Set Angle and Hallux Alignment in Patients Undergoing Tarsometatarsal Arthrodesis for Hallux Abducto Valgus: A Case Series and Critical Review of the Literature," The Journal of Foot and Ankle Surgery, vol. 52, No. 3, May/Jun. 2013, pp. 348-354.

Dayton et al., "Quantitative Analysis of the Degree of Frontal Rotation Required to Anatomically Align the First Metatarsal Phalangeal Joint During Modified Tarsal-Metatarsal Arthrodesis Without Capsular Balancing," The Journal of Foot and Ankle Surgery, 2015, pp. 1-6.

De Geer et al., "A New Measure of Tibial Sesamoid Position in Hallux Valgus in Relation to the Coronal Rotation of the First Metatarsal in CT Scans," Foot and Ankle International, Mar. 26, 2015, 9 pages.

DiDomenico et al., "Correction of Frontal Plane Rotation of Sesamoid Apparatus during the Lapidus Procedure: A Novel Approach," The Journal of Foot and Ankle Surgery, vol. 53, 2014, pp. 248-251.

Dobbe et al. "Patient-Tailored Plate for Bone Fixation and Accurate 3D Positioning in Corrective Osteotomy," Medical and Biological Engineering and Computing, vol. 51, No. 1-2, Feb. 2013, pp. 19-27, (Abstract Only).

EBI Extra Small Rail Fixator, Biomet Trauma, retrieved Dec. 19, 2014, from the Internet: <http://footandanklefixation.com/product/biomet-trauma-ebi-extra-small-rail-fixator>, 7 pages.

Garthwait, "Accu-Cut System Facilitates Enhanced Precision," Podiatry Today, vol. 18, No. 6, Jun. 2005, 6 pages.

Gonzalez Del Pino et al., "Variable Angle Locking Intercarpal Fusion System for Four-Corner Arthrodesis: Indications and Surgical Technique," Journal of Wrist Surgery, vol. 1, No. 1, Aug. 2012, pp. 73-78.

Grondal et al., "A Guide Plate for Accurate Positioning of First Metatarsophalangeal Joint during Fusion," Operative Orthopädie Und Traumatologie, vol. 16, No. 2, 2004, pp. 167-178 (Abstract Only).

"HAT-TRICK Lesser Toe Repair System," Smith & Nephew, Brochure, Aug. 2014, 12 pages.

"Hoffmann II Compact External Fixation System," Stryker, Brochure, Literature No. 5075-1-500, 2006, 12 pages.

"Hoffmann II Micro Lengthener," Stryker, Operative Technique, Literature No. 5075-2-002, 2008, 12 pages.

"Hoffmann Small System External Fixator Orthopedic Instruments," Stryker, retrieved Dec. 19, 2014, from the Internet: <http://www.alibaba.com/product-detail/Stryker-Hoffmann-Small-System-External-Fixator_1438850129.html>, 3 pages.

Kim et al., "A New Measure of Tibial Sesamoid Position in Hallux Valgus in Relation to the Coronal Rotation of the First Metatarsal in CT Scans," Foot and Ankle International, vol. 36, No. 8, 2015, pp. 944-952.

"Lag Screw Target Bow," Stryker Leibinger GmbH & Co. KG, Germany 2004, 8 pages.

MAC (Multi Axial Correction) Fixation System, Biomet Trauma, retrieved Dec. 19, 2014, from the Internet: <http://footandanklefixation.com/product/biomet-trauma-mac-multi-axial-correction-fixation-system>, 7 pages.

Michelangelo Bunion System, Surgical Technique, Instratek Incorporated, publication date unknown, 4 pages.

Mini Joint Distractor, Arthrex, retrieved Dec. 19, 2014, from the Internet: <http://www.arthrex.com/foot-ankle/mini-joint-distractor/products>, 2 pages.

MiniRail System, Small Bone Innovations, Surgical Technique, 2010, 24 pages.

Modular Rail System: External Fixator, Smith & Nephew, Surgical Technique, 2013, 44 pages.

Monnich et al., "A Hand Guided Robotic Planning System for Laser Osteotomy in Surgery," World Congress on Medical Physics and Biomedical Engineering vol. 25/6: Surgery, Nimimal Invasive Interventions, Endoscopy and Image Guided Therapy, Sep. 7-12, 2009, pp. 59-62, (Abstract Only).

Moore et al., "Effect of Ankle Flexion Angle on Axial Alignment of Total Ankle Replacement," Foot and Ankle International, vol. 31, No. 12, Dec. 2010, pp. 1093-1098, (Abstract Only).

Mortier et al., "Axial Rotation of the First Metatarsal Head in a Normal Population and Hallux Valgus Patients," Orthopaedics and Traumatology: Surgery and Research, vol. 98, 2012, pp. 677-683.

Okuda et al., "Postoperative Incomplete Reduction of the Sesamoids as a Risk Factor for Recurrence of Hallux Valgus," The Journal of Bone and Joint Surgery, vol. 91-A, No. 1, Jul. 2009, pp. 1637-1645.

Rx-Fix Mini Rail External Fixator, Wright Medical Technology, Brochure, Aug. 15, 2014, 2 pages.

Scanlan et al. "Technique Tip: Subtalar Joint Fusion Using a Parallel Guide and Double Screw Fixation," The Journal of Foot and Ankle Surgery, vol. 49, Issue 3, May-Jun. 2010, pp. 305-309, (Abstract Only).

Scranton Jr. et al, "Anatomic Variations in the First Ray: Part I. Anatomic Aspects Related to Bunion Surgery," Clinical Orthopaedics and Related Research, vol. 151, Sep. 1980, pp. 244-255.

Siddiqui et al. "Fixation of Metatarsal Fracture With Bone Plate in a Dromedary Heifer," Open Veterinary Journal, vol. 3, No. 1, 2013, pp. 17-20.

Sidekick Stealth Rearfoot Fixator, Wright Medical Technology, Surgical Technique, Dec. 2, 2013, 20 pages.

Simpson et al., "Computer-Assisted Distraction Ostegogenesis by Ilizarov's Method," International Journal of Medical Robots and Computer Assisted Surgery, vol. 4, No. 4, Dec. 2008, pp. 310-320, (Abstract Only).

Small Bone External Fixation System, Acumed, Surgical Technique, Effective date Sep. 2014, 8 pages.

Stableloc External Fixation System, Acumed, Product Overview, Effective date Sep. 2015, 4 pages.

Stahl et al., "Derotation of Post-Traumatic Femoral Deformities by Closed Intramedullary Sawing," Injury, vol. 37, No. 2, Feb. 2006, pp. 145-151, (Abstract Only).

(56) References Cited

OTHER PUBLICATIONS

Talbot et al.,"Assessing Sesamoid Subluxation: How Good is the AP Radiograph?," Foot and Ankle International, vol. 19, No. 8, Aug. 1998, pp. 547-554.
TempFix Spanning the Ankle Joint Half Pin and Transfixing Pin Techniques, Biomet Orthopedics, Surgical Technique, 2012, 16 pages.
Weber et al., "A Simple System for Navigation of Bone Alignment Osteotomies of the Tibia," International Congress Series, vol. 1268, Jan. 2004, pp. 608-613, (Abstract Only).
Whipple et al., "Zimmer Herbert Whipple Bone Screw System: Surgical Techniques for Fixation of Scaphoid and Other Small Bone Fractures," Zimmer, 2003, 59 pages.
Yakacki et al. "Compression Forces of Internal and External Ankle Fixation Devices with Simulated Bone Resorption," Foot and Ankle International, vol. 31, No. 1, Jan. 2010, pp. 76-85, (Abstract Only).
Yasuda et al., "Proximal Supination Osteotomy of the First Metatarsal for Hallux Valgus," Foot and Ankle International, vol. 36, No. 6, Jun. 2015, pp. 696-704.
Dayton et al."Evidence-Based Bunion Surgery: A Critical Examination of Current and Emerging Concepts and Techniques," Springer International Publishing, 2017, 254 pages.
Joung et al., "A spherical bone cutting system for Rotational Acetabular Osteotomy," World Congress on Medical Physics and Biomedical Engineering, 2006, pp. 3130-3133 (Abstract Only).
Koyama et al., "Computer-assisted spherical osteotomy with a curved-bladed Tuke Saw®," Computer Aided Surgery, vol. 11, No. 4, Jul. 2006, pp. 202-208.
Sakuma et al., "A bone cutting device for rotational acetabular osteotomy (RAO) with a curved oscillating saw," International Congress Series, vol. 1268, 2004, pp. 632-637.
Weil Foot & Ankle Institute, "Scarf Akin Procedure for Bunion Correction," YouTube video, published on Jul. 29, 2008 to https://www.youtube.com/watch?v=Sh2V8QvbaGc, 4 pages of example screen shots.
"Accu-Cut Osteotomy Guide System," BioPro, Brochure, Oct. 2018, 2 pages.
"Acumed Osteotomiesystem Operationstechnik," Acumed, 2014, 19 pages (including 3 pages English translation).
Blomer, "Knieendoprothetik—Herstellerische Probleme und technologische Entwicklungen," Orthopade, vol. 29, 2000, pp. 688-696, including English Abstract on p. 689.
Bouaicha et al., "Fixation of Maximal Shift Scarf Osteotomy with Inside-Out Plating: Technique Tip," Foot & Ankle International, vol. 32, No. 5, May 2011, pp. 567-569.
"Futura Forefoot Implant Arthroplasty Products," Tornier, Inc., 2008, 14 pages.
Gotte, "Entwicklung eines Assistenzrobotersystems für die Knieendoprothetik," Forschungsberichte, Technische Universitat Munchen, 165, 2002, 11 pages, including partial English Translation.
Gregg et al., "Plantar plate repair and Weil osteotomy for metatarsophalangeal joint instability," Foot and Ankle Surgery, vol. 13, 2007, pp. 116-121.
"Hat-Trick Lesser Toe Repair System, Foot and Ankle Technique Guide, Metatarsal Shortening Osteotomy Surgical Technique," Smith & Nephew, 2014, 16 pages.
Hetherington et al., "Evaluation of surgical experience and the use of an osteotomy guide on the apical angle of an Austin osteotomy," The Foot, vol. 18, 2008, pp. 159-164.

Hirao et al., "Computer assisted planning and custom-made surgical guide for malunited pronation deformity after first metatarsophalangeal joint arthrodesis in rheumatoid arthritis: A case report," Computer Aided Surgery, vol. 19, Nos. 1-3, 2014, pp. 13-19.
Lieske et al., "Implantation einer Sprunggelenktotalendo-prothese vom Typ Salto 2," Operative Orthopadie und Traumatologie, vol. 26, No. 4, 2014, pp. 401-413, including English Abstract on p. 403.
Magin, "Computemavigierter Gelenkersatz am Knie mit dem Orthopilot," Operative Orthopadie und Traumatologie, vol. 22, No. 1, 2010, pp. 63-80, including English Abstract on p. 64.
Magin, "Die belastungsstabile Lapidus-Arthrodese bei Hallux-valgus-Deformitat mittels IVP-Plattenfixateur (V-TEK-System)," Operative Orthopädie und Traumatologie, vol. 26, No. 2, 2014, pp. 184-195, including English Abstract on p. 186.
Miyake et al., "Three-Dimensional Corrective Osteotomy for Malunited Diaphyseal Forearm Fractures Using Custom-Made Surgical Guides Based on Computer Simulation," JBJS Essential Surgical Techniques, vol. 2, No. 4, 2012, 11 pages.
Nagy et al., "The AO Ulnar Shortening Osteotomy System Indications and Surgical Technique," Journal of Wrist Surgery, vol. 3, No. 2, 2014, pp. 91-97.
NexFix from Nexa Orthopedics, MetaFix I from Merete Medical, Inc. and The BioPro Lower Extremities from BioPro, found in Foot & Ankle International Journal, vol. 28, No. 1, Jan. 2007, 4 pages.
Odenbring et al., "A guide instrument for high tibial osteotomy," Acta Orthopaedica Scandinavica, vol. 60, No. 4, 1989, pp. 449-451.
Otsuki et al., "Developing a novel custom cutting guide for curved per-acetabular osteotomy," International Orthopaedics (SICOT), vol. 37, 2013, pp. 1033-1038.
"Patient to Patient Precision, Accu-Cut, Osteotomy Guide System," BioPro, Foot & Ankle International Journal, vol. 23, No. 8, Aug. 2002, 2 pages.
Peters et al., "Flexor Hallucis Longus Tendon Laceration as a Complication of Total Ankle Arthroplasty," Foot & Ankle International, vol. 34, No. 1, 2013, pp. 148-149.
"Prophecy Inbone Preoperative Navigation Guides," Wright Medical Technology, Inc., Nov. 2013, 6 pages.
"Rayhack Ulnar Shortening Generation II Low-Profile Locking System Surgical Technique," Wright Medical Technology, Inc., Dec. 2013, 20 pages.
Saltzman et al., "Prospective Controlled Trial of Star Total Ankle Replacement Versus Ankle Fusion: Initial Results," Foot & Ankle International, vol. 30, No. 7, Jul. 2009, pp. 579-596.
"Smith & Nephew scores a Hat-Trick with its entry into the high-growth hammer toe repair market," Smith & Nephew, Jul. 31, 2014, 2 pages.
Tricot et al., "3D-corrective osteotomy using surgical guides for posttraumatic distal humeral deformity," Acta Orthopaedica Belgica, vol. 78, No. 4, 2012, pp. 538-542.
Vitek et al., "Die Behandlung des Hallux rigidus mit Cheilektomie und Akin-Moberg-Osteotomie unter Verwendung einer neuen Schnittlehre und eines neuen Schraubensystems," Orthopadische Praxis, vol. 44, Nov. 2008, pp. 563-566, including English Abstract on p. 564.
Vitek, "Neue Techniken in der Fußchirurgie Das V-tek-System," ABW Wissenschaftsverlag GmbH, 2009, 11 pages, including English Abstract.
Weil et al., "Anatomic Plantar Plate Repair Using the Weil Metatarsal Osteotomy Approach," Foot & Ankle Specialist, vol. 4, No. 3, 2011, pp. 145-150.
Wendl et al., "Navigation in der Knieendoprothetik," OP-Journal, vol. 17, 2002, pp. 22-27, including English Abstract.

\* cited by examiner

OSTEOTOMY PROCEDURE FOR CORRECTING BONE MISALIGNMENT

CROSS-REFERENCE

This application claims the benefit of U.S. Provisional Patent Application No. 62/380,074, filed Aug. 26, 2016, the entire contents of which are incorporated herein by reference.

TECHNICAL FIELD

This disclosure relates to devices and techniques for correcting bones and, more particularly, to osteotomy techniques for correcting bone misalignment.

BACKGROUND

Bones, such as the bones of a foot, may be anatomically misaligned. In certain circumstances, surgical intervention is required to correctly align the bones to reduce patient discomfort and improve patient quality of life.

SUMMARY

In general, this disclosure is directed to devices and techniques for correcting an anatomical misalignment of one or more bones. In some examples, the technique involves making a generally crescent-shaped cut transecting a bone to form a concave-shaped end and a convex-shaped end. The two resulting bone portions can be distracted, or separated from each other, and a second cut performed on the concave-shaped end of the resulting bone portion. The second cut may also be a generally crescent-shaped cut but may be angled with respect to the concavity resulting from the first cut. For example, the first generally crescent-shaped cut may form a saddle and the second generally crescent-shaped cut may form an intersecting and offset saddle on a bone portion. The corresponding convex bone portion may be moved in multiple planes to adjust the alignment of the bone portion. For example the convex bone portion may be moved from the first saddle to the adjacent second saddle thereby facilitating realignment of the bone portion.

As one example, the technique may be performed on a first metatarsal to correct a bone alignment deformity, such as a bunion deformity. A first generally crescent-shaped cut can be made parallel to or at an offset angle relative to a frontal plane of the metatarsal transecting the metatarsal into two portions: one portion having a convex-shaped end and an opposed portion having a concave-shaped end. A second crescent shape cut may be made at an angle relative to a transverse plane bisecting the portion of the metatarsal having a convex-shaped end. This second cut may chamfer or remove a portion of the convex-shaped bone end, such as a dorsal lateral quadrant of the bone end. This can facilitate subsequent realignment of the concave-shaped end of the opposing bone portion relative to the convex-shaped end.

In another alternative, a bone realignment technique may be performed by making a single generally crescent-shaped cut instead of two generally crescent-shaped cuts. In this technique, a generally crescent-shaped cut can be made parallel to or at an offset angle relative to a frontal plane of the metatarsal transecting the metatarsal into a portion having a convex-shaped end and an opposed portion having a concave-shaped end. A planar, transverse cut can then be made across the bone portion having the convex-shaped end resulting in three bone portions: a bone portion having a concave-shaped end, a bone portion having a planar end, and an intermediate bone portion having one planar end and one convex-shaped end. The intermediate bone portion can be translated along the arc of the curve formed by the concave-shaped end to reorient the metatarsal in the transverse plane. The bone portion having the planar end can also be rotated relative to the intermediate portion in the frontal plane. After suitably reorienting the three bone portions relative to each other, three bone portions can be fixated together.

In other applications, a bone realignment technique may be performed without requiring multiple cuts. In these applications, a generally spherical-shaped cutting member can be used to transect the bone being realigned. For example, a generally spherical-shaped cutting device can be used to transect a first metatarsal resulting in a one bone portion having a generally spherical-shaped projection and an opposed bone portion having a generally spherical-shaped socket. The two bone portions can then be reoriented in multiple planes relative to each other with or without performing additional cuts on a bone portion. In either case, after suitably realigning one bone portion relative to another bone portion, the bone portions may be permanently fixated to each other. For example, using plates, screws, pins and/or other fixation hardware, one bone portion may be fixed to the opposed bone portion.

In yet further applications, a bone realignment technique may be performed by transecting a bone with a substantially linear (e.g., non-curved) cutting member by making a transverse cut across the bone. For example, a planar saw blade can be used to transect a first metatarsal resulting in a first bone portion and separate second bone portion that each have planar cut end faces. The two bone portions can then be reoriented in multiple planes relative to each other with or without performing additional cuts on a bone portion. After suitably realigning one bone portion relative to another bone portion, the bone portions may be permanently fixated to each other. For example, using plates, screws, pins and/or other fixation hardware, one bone portion may be fixed to the opposed bone portion.

Independent of the specific cutting technique or shape of cutting instrument used to cut the bone into two portions for realignment, a distal bone portion may be realigned relative to a proximal bone portion in multiple planes with or without the use of intra-operative fluoroscopy. In some examples, the clinician uses fluoroscopic imaging to visually assist in and/or guide realignment of the distal bone portion relative to the proximal bone portion. The relative position and/or degree of angular rotation of the distal bone portion relative to the proximal bone portion can be viewed by the clinician under fluoroscopic imaging and used to guide the degree of realignment. The clinician may view the movement of the distal bone portion relative to the proximal bone portion continuously while making the realignment or at one or more intervals to check the realignment made or being made. The clinician may use various anatomical landmarks visible via fluoroscopy, such as the rotational position of the distal metatarsal head and/or the position of the sesamoid bones to help determine when the distal bone portion is suitably realigned.

In some examples, the clinician may introduce one or more pins into the distal bone portion and/or proximal bone portion to help facilitate realignment. For example, the clinician may insert a first pin in a distal bone portion and a second pin in a proximal bone portion. The clinician can use the one or more pins as a grasping element, e.g., by grasping an inserted pin and using the pin to manipulate and control movement of the distal bone portion relative to the proximal bone portion. The clinician may or may not monitor the relative position and/or degree of angular rotation of the one or more pins during movement to help set the desired degree of realignment of the distal portion relative to the proximal portion. For example, the clinician may monitor the relative position and/or degree of angular rotation between a pin inserted into the proximal bone portion and another pin inserted in the distal bone portion during realignment to help set the desired degree of realignment of the distal portion relative to the proximal portion. The clinician can monitor the position of the pin(s) visually (e.g., with the unaided eye) and/or using fluoroscopic imaging.

In one example, a method is described that involves making a first crescentic-shaped cut transecting a first metatarsal, thereby forming a first metatarsal portion having a concave-shaped end and a second metatarsal portion having a convex-shaped end. The method further involves making a second crescentic-shaped cut across the concave-shaped end of the first metatarsal portion. In addition, the method includes moving the second metatarsal portion in at least two planes relative to the first metatarsal portion, thereby adjusting an anatomical alignment of the second metatarsal portion.

In another example, a method is described that includes making a spherical-shaped cut transecting a first metatarsal, thereby forming a first metatarsal portion having a spherical-shaped projection and a second metatarsal portion having a generally spherical-shaped recess. The method also involves moving the second metatarsal portion in at least two planes relative to the first metatarsal portion, thereby adjusting an anatomical alignment of the second metatarsal portion.

In another example, a method is described that includes making a crescentic-shaped cut transecting a first metatarsal, thereby forming a first metatarsal portion having a concave-shaped end and a second metatarsal portion having a convex-shaped end. The method also involves making a planar cut across the second metatarsal portion and offset from the concave-shaped end or the convex-shaped end, thereby forming a planar end on the second metatarsal portion and an intermediate bone portion having the convex-shaped end. In addition, the method includes moving the second metatarsal portion relative to the first metatarsal portion and the intermediate bone portion, thereby adjusting an anatomical alignment of the second metatarsal portion.

The details of one or more examples are set forth in the accompanying drawings and the description below. Other features, objects, and advantages will be apparent from the description and drawings, and from the claims.

DETAILED DESCRIPTION

In general, the present disclosure is directed to devices and techniques for correcting a misalignment of one or more bones. The disclosed devices and techniques can be implemented in an osteotomy procedure in which a bone is surgically cut and/or a piece of bone is surgically removed. In some examples, the technique is performed on one or more bones in the foot or hand, where bones are relatively small compared to bones in other parts of the human anatomy. For example, the foregoing description generally refers to example techniques performed on the foot and, more particularly a metatarsal of the foot. However, the disclosed techniques may be performed on other bones, such as the tibia, fibula, ulna, humerus, femur, or yet other bone, and the disclosure is not limited in this respect unless otherwise specifically indicated. In some applications, however, the disclosed techniques are used to correct a misalignment between a metatarsal (e.g., a first metatarsal) and a second metatarsal and/or a cuneiform (e.g., a medial, or first, cuneiform), such as in a bunion correction surgery.

Figure 1B:
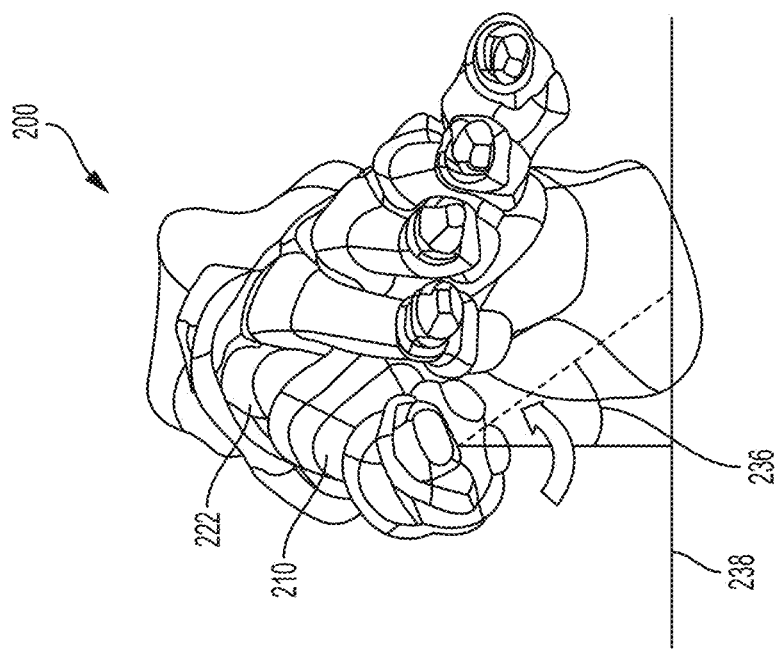
FIGS. 1A and 1B are front views of a foot showing a normal first metatarsal position and an example frontal plane rotational misalignment position, respectively.
Figure 1A:
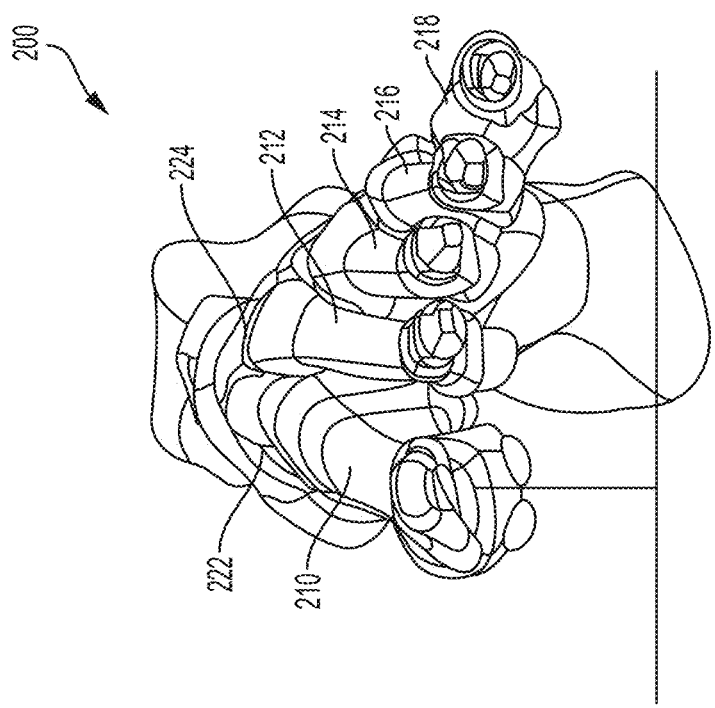
Figure 2B:
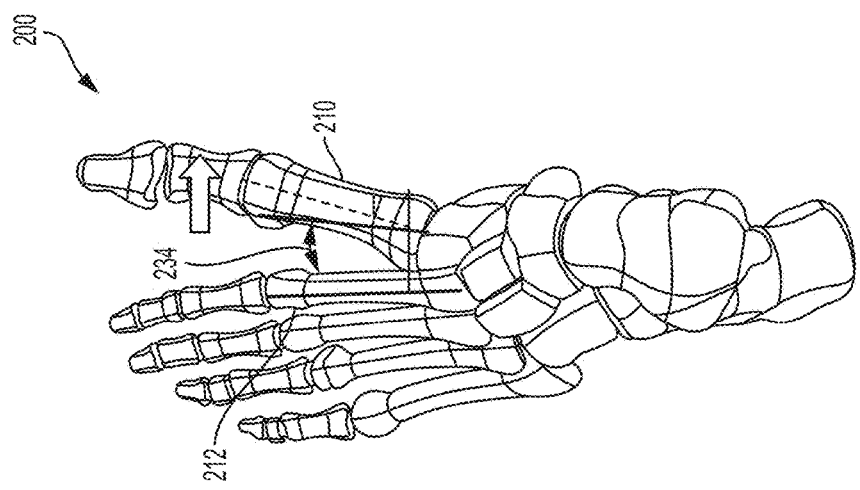
FIGS. 2A and 2B are top views of a foot showing a normal first metatarsal position and an example transverse plane misalignment position, respectively.
Figure 2A:
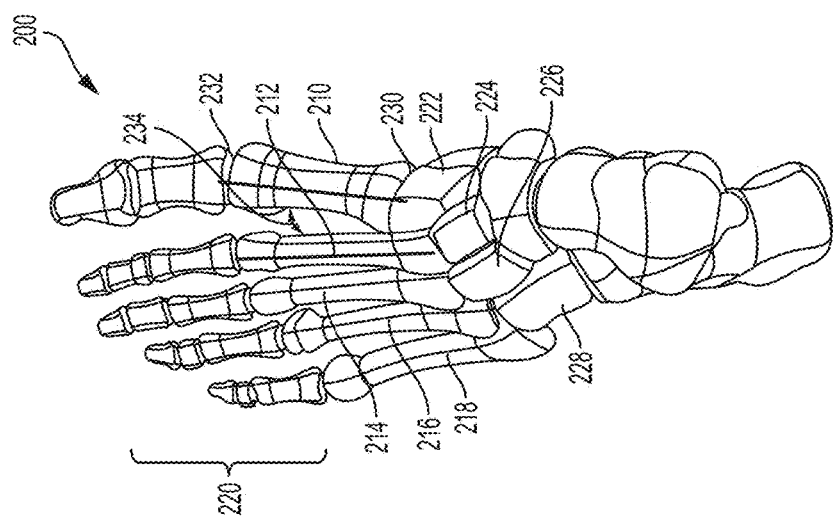
Figure 3B:
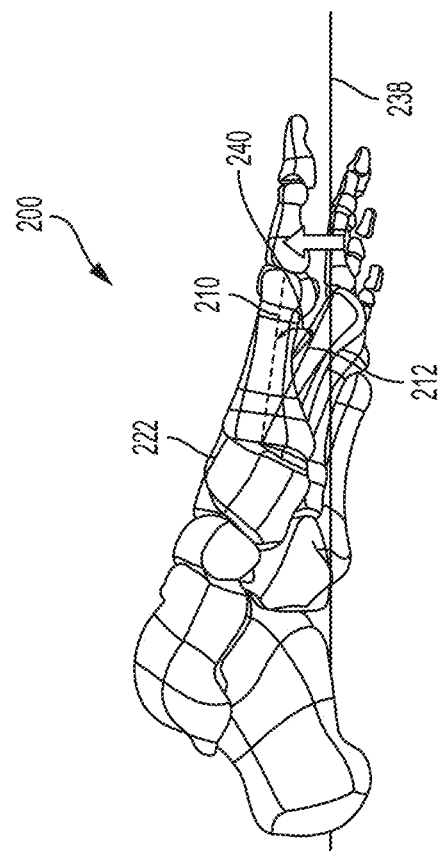
FIGS. 3A and 3B are side views of a foot showing a normal first metatarsal position and an example sagittal plane misalignment position, respectively.
Figure 3A:
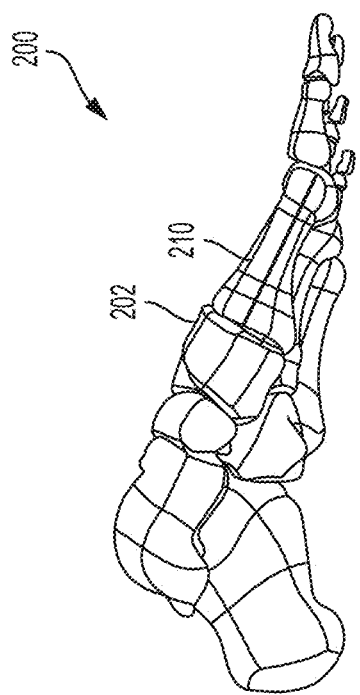

FIGS. 1-3 are different views of a foot 200 showing example anatomical misalignments that may occur and be corrected according to the present disclosure. Such misalignment may be caused by a hallux valgus (bunion), natural growth deformity, or other condition causing anatomical misalignment. FIGS. 1A and 1B are front views of foot 200 showing a normal first metatarsal position and an example frontal plane rotational misalignment position, respectively. FIGS. 2A and 2B are top views of foot 200 showing a normal first metatarsal position and an example transverse plane misalignment position, respectively. FIGS. 3A and 3B are side views of foot 200 showing a normal first metatarsal position and an example sagittal plane misalignment position, respectively. While FIGS. 1B, 2B, and 3B show each respective planar misalignment in isolation, in practice, a metatarsal may be misaligned in any two of the three planes or even all three planes. Accordingly, it should be appreciated that the depiction of a single plane misalignment in each of FIGS. 1B, 2B, and 3B is for purposes of illustration and a metatarsal may be misaligned in multiple planes that is desirably corrected.

With reference to FIGS. 1A and 2A, foot 200 is composed of multiple bones including a first metatarsal 210, a second metatarsal 212, a third metatarsal 214, a fourth metatarsal 216, and a fifth metatarsal 218. The metatarsals are connected distally to phalanges 220 and, more particularly, each to a respective proximal phalanx. The first metatarsal 210 is connected proximally to a medial cuneiform 222, while the second metatarsal 212 is connected proximally to an intermediate cuneiform 224 and the third metatarsal is connected proximally to lateral cuneiform 226. The fourth and fifth metatarsals 216, 218 are connected proximally to the cuboid bone 228. The joint 230 between a metatarsal and respective cuneiform (e.g., first metatarsal 210 and medial cuneiform 222) is referred to as the tarsometatarsal ("TMT") joint. The joint 232 between a metatarsal and respective proximal phalanx is referred to as a metatarsophalangeal joint. The angle 234 between adjacent metatarsals (e.g., first metatarsal 210 and second metatarsal 212) is referred to as the intermetatarsal angle ("IMA").

As noted, FIG. 1A is a frontal plane view of foot 200 showing a typical position for first metatarsal 210. The frontal plane, which is also known as the coronal plane, is generally considered any vertical plane that divides the body into anterior and posterior sections. On foot 200, the frontal plane is a plane that extends vertically and is perpendicular to an axis extending proximally to distally along the length of the foot. FIG. 1A shows first metatarsal 210 in a typical rotational position in the frontal plane. FIG. 1B shows first metatarsal 210 with a frontal plane rotational deformity characterized by a rotational angle 236 relative to ground, as indicated by line 238.

FIG. 2A is a top view of foot 200 showing a typical position of first metatarsal 210 in the transverse plane. The transverse plane, which is also known as the horizontal plane, axial plane, or transaxial plane, is considered any plane that divides the body into superior and inferior parts. On foot 200, the transverse plane is a plane that extends horizontally and is perpendicular to an axis extending dorsally to plantarly (top to bottom) across the foot. FIG. 2A shows first metatarsal 210 with a typical IMA 234 in the transverse plane. FIG. 2B shows first metatarsal 210 with a transverse plane rotational deformity characterized by a greater IMA caused by the distal end of first metatarsal 210 being pivoted medially relative to the second metatarsal 212.

FIG. 3A is a side view of foot 200 showing a typical position of first metatarsal 210 in the sagittal plane. The sagittal plane is a plane parallel to the sagittal suture which divides the body into right and left halves. On foot 200, the sagittal plane is a plane that extends vertically and is perpendicular to an axis extending proximally to distally along the length of the foot. FIG. 3A shows first metatarsal 210 with a typical rotational position in the sagittal plane. FIG. 3B shows first metatarsal 210 with a sagittal plane rotational deformity characterized by a rotational angle 240 relative to ground, as indicated by line 238.

A bone positioning technique according to the disclosure can be useful to correct an anatomical misalignment of a bones or bones. In some applications, the technique involves realigning a metatarsal or a portion thereof, relative to an adjacent cuneiform and/or adjacent metatarsal. The metatarsal undergoing realignment may be anatomically misaligned in the frontal plane, transverse plane, and/or sagittal plane, as illustrated and discussed with respect to FIGS. 1-3 above. Accordingly, realignment may involve releasing the misaligned metatarsal or portion thereof for realignment and thereafter realigning the metatarsal or portion in one or more planes, two or more planes, or all three planes. After suitably realigning the metatarsal or portion thereof, the metatarsal or portion thereof can be fixated to hold and maintain the realigned positioned.

While a metatarsal can have a variety of anatomically aligned and misaligned positions, in some examples, the term "anatomically aligned position" means that an angle of a long axis of first metatarsal 210 relative to the long axis of second metatarsal 212 is about 10 degrees or less in the transverse plane and/or sagittal plane. In certain embodiments, anatomical misalignment can be corrected in both the transverse plane and the frontal plane. In the transverse plane, a normal IMA 234 between first metatarsal 210 and second metatarsal 212 is less than about 9 degrees. An IMA 234 of between about 9 degrees and about 13 degrees is considered a mild misalignment of the first metatarsal and the second metatarsal. An IMA 234 of greater than about 16 degrees is considered a severe misalignment of the first metatarsal and the second metatarsal. In some embodiments, methods according to the disclosure are utilized to anatomically align first metatarsal 210 or a portion thereof by reducing the IMA from over 10 degrees to about 10 degrees or less (e.g., to an IMA of about 1-5 degrees), including to negative angles of about −5 degrees or until interference with the second metatarsal, by positioning the first metatarsal at a different angle with respect to the second metatarsal.

With respect to the frontal plane, a normal first metatarsal will be positioned such that its crista prominence is generally perpendicular to the ground and/or its sesamoid bones are generally parallel to the ground and positioned under the metatarsal. This position can be defined as a metatarsal rotation of 0 degrees. In a misaligned first metatarsal, the metatarsal is axially rotated between about 4 degrees to about 30 degrees or more. In some embodiments, methods according to the disclosure are utilized to anatomically align the metatarsal by reducing the metatarsal rotation from about 4 degrees or more to less than 4 degrees (e.g., to about 0 to 2 degrees) by rotating the metatarsal with respect to the medial cuneiform.

Figure 4A:
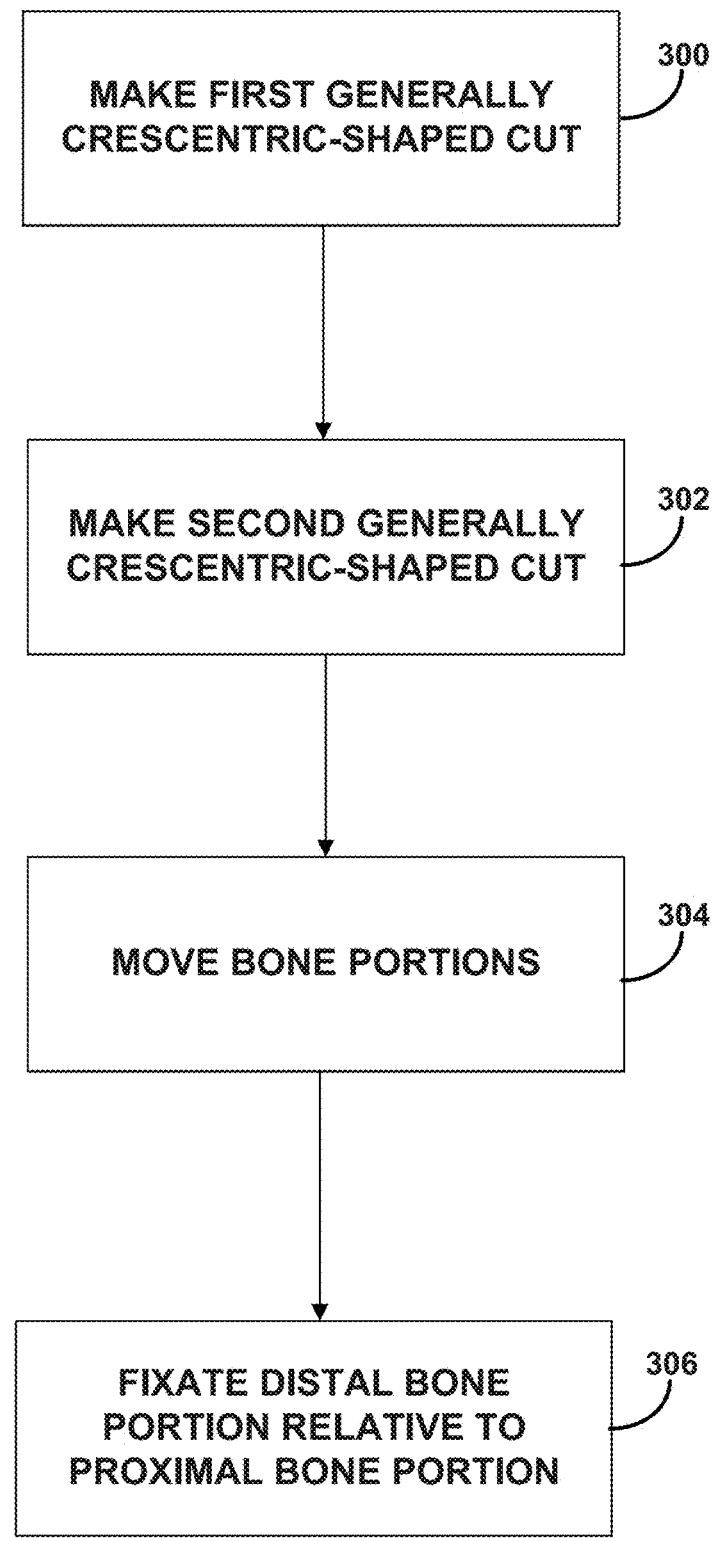
FIGS. 4A-4D are flow diagrams illustrating example osteotomy techniques for correcting an anatomical alignment.

FIG. 4A is a flow diagram illustrating an example osteotomy technique for correcting an anatomical alignment. The technique will be described with respect to first metatarsal 210 although can be performed on other bones, as discussed above. With reference to FIG. 4A, the example technique involves making a first crescentic-shaped cut transecting metatarsal 210 (300). The first cut separates the first metatarsal 210 into two portions: a proximal portion and a distal portion. One of the portions can have a concave-shaped end with a radius corresponding to the radius of the crescentic-shaped cut while the other portion can have a corresponding concave-shaped end of the same radius. The two portions can be distracted, or separated by force, to provide opposed ends separated from each other.

The technique of FIG. 4A further involves making a second crescentic-shaped cut across the concave-shaped end of the concave-shaped bone portion (302). The second crescentic-shaped cut can be made at an offset angle relative to the first crescentic-shaped cut, providing intersecting cut arcs that define multiple intersecting concave regions on the end face of the bone. For example, second crescentic-shaped cut may be used to chamfer a dorsal-lateral quadrant of the concave-shaped bone portion, providing a second concave pocket offset from a centered concavity formed upon making the first crescentic-shaped cut. This second concave pocket may provide a region in which the convex-shaped end of the opposite bone portion can be rotated into to rotationally realign one bone portion relative to the other bone portion.

For example, the illustrated technique includes moving one bone portion relative to another bone portion to adjust an alignment of the bone portions relative to each other (304). In some examples, the distal portion of the transected first metatarsal 210 is rotated relative to the proximal portion of the transected metatarsal. The distal portion of the transected first metatarsal 210 may be rotated in the frontal plane and/or pivoted in the transverse plane and/or pivoted in the sagittal plane to help correct an anatomical misalignment of the distal portion of the metatarsal. In some examples, the distal portion of the first metatarsal 210 is rotated about an axis extending through the frontal plane so the medial side is moved dorsally and/or the distal portion of the first metatarsal 210 is moved laterally in the transverse plane and/or plantarly in the sagittal plane. For example, the distal portion of the transected first metatarsal 210 may be moved from an anatomically misaligned position relative to second metatarsal 212 and/or the medial cuneiform 222 to an anatomically aligned position. During movement, the end face of the distal portion of the first metatarsal 210 created by making the first crescentic-shaped cut can shift relative to the end face of the proximal portion of the first metatarsal created by making the cut.

In some example, the end face of the distal portion of the first metatarsal 210 created by making the first crescentic-shaped moves medially relative to the end face of the proximal portion of the first metatarsal created by making the cut. This base shift can cause the lateral side of the distal portion to move from being aligned with the lateral side of the proximal portion to being medially offset relative to the lateral face. For example, the lateral side of the distal portion of first metatarsal 210 may move into a concave pocket formed in the medial-lateral quadrant of the end face of the proximal portion of the first metatarsal by making the second crescentic-shaped cut. In these applications, the second pocket formed by making the second crescentic-shaped cut may reduce or eliminate bone-on-bone interference that may otherwise occur between the proximal and distal portions of the first metatarsal during realignment.

After suitably moving the two transected bone portions relative to each other, the bone portions can be fixated to each other to secure and hold the new realigned position achieved through movement (306). The bone portions can be fixated using pins, plates, screws, or other fixation devices to provide stability during the healing process. In one example, a bone plate is secured on the dorsal-medial side of the distal and proximal bone portions across the joint formed by transecting the first metatarsal 210 into the two bone portions. Additionally or alternatively, a bone plate may be secured on a different portion of the bones, such as helical bone plate that extends from a medial side of the distal bone portion to a plantar side of the proximal bone portion and/or from a plantar side of the distal bone portion to a medial side of the proximal bone portion. Additional details on example bone plating configurations that can be used are described in U.S. patent application Ser. No. 14/990,368, entitled "BONE PLATING SYSTEM AND METHOD" and filed on Jan. 7, 2016, the entire contents of which are incorporated herein by reference.

Figure 4B:
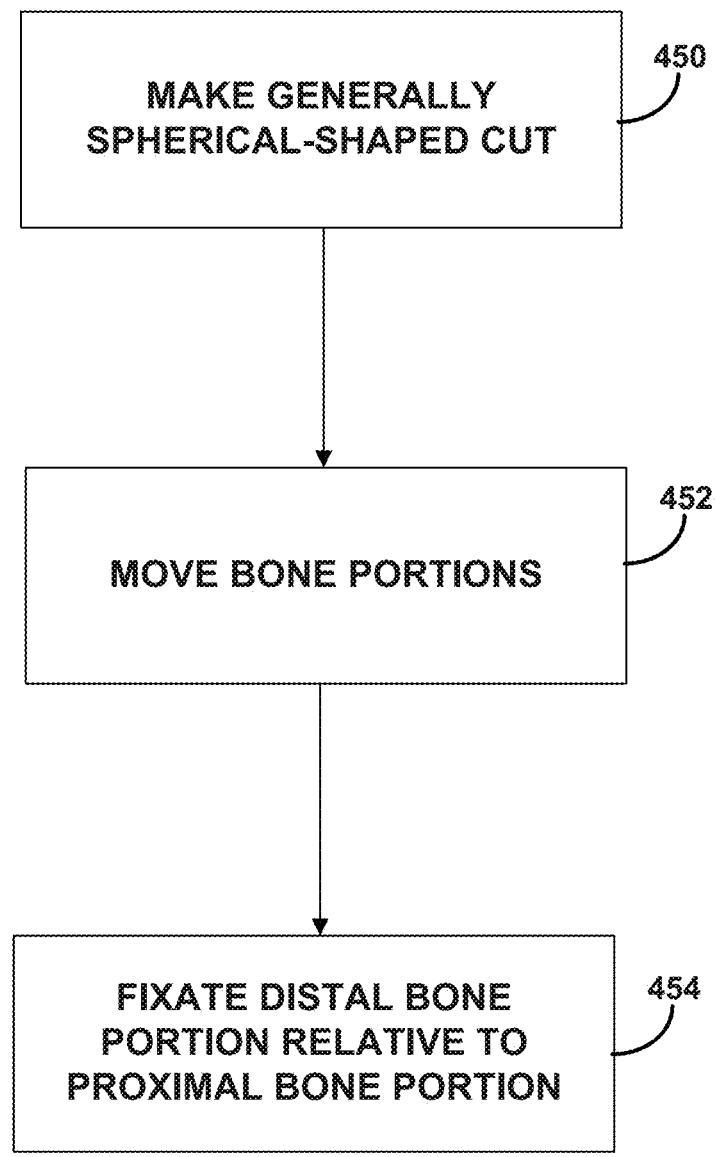

FIG. 4B is a flow diagram illustrating another example technique for correcting an anatomical alignment. The example technique involves making a generally spherical-shaped cut transecting a metatarsal 210 (450). The generally spherical-shaped cut separates the first metatarsal 210 into two portions: a proximal portion and a distal portion. One of the portions can have a generally spherical-shaped end while the end of the opposed bone portion can have a corresponding generally spherical-shaped socket.

To make the generally spherical-shaped cut, a generally spherical-shaped cutting instrument can be translated through an arc that transects the first metatarsal. The cutting instrument can be translated in any direction across the metatarsal, including from the dorsal to the plantar side of the metatarsal or vice versa, or the medial to the lateral side of the metatarsal or vice versa. The cutting instrument can be translated across the metatarsal such that the resulting proximal portion defines the generally spherical-shaped ball and the distal portion defines the corresponding generally spherical-shaped socket. Alternatively, the cutting instrument can be translated across the metatarsal such that the resulting distal portion defines the generally spherical-shaped ball and the proximal portion defines the corresponding generally spherical-shaped socket.

The generally spherical-shaped ends formed by making the transecting cut according to the technique of FIG. 4B may have a substantially constant radius (or, in some embodiments, constant radius) of curvature from a geometric center of the shape or may have a radius of curvature that varies across the face from the geometric center of the shape. For example, the generally spherical-shaped ends may have a parabolic or other spheroidal shape that provides one rounded end that fits into a cup-like depression of an opposed end. The generally spherical-shaped ends can be achieved using a cutting instrument with a generally spherical-shaped blade or cutting instruments having alternative shapes that are moved through the bone during transection to achieve the general spherical-shape. In some examples, a generally spherical-shaped cutting instrument is used that has a generally spherical-shaped cutting blade having a diameter ranging from 6 millimeters to 30 millimeters, although cutting blades of other dimensions can also be used. The radius of curvature of the generally spherical-shaped cutting blade may be constant across the blade or may vary by less than a threshold amount, such as plus or minus 30%, plus or minus 20%, plus or minus 10%, plus or minus 5%, or plus or minus 1%.

After cutting the first metatarsal into two portions using a generally spherical-shaped cutting instrument, the technique of FIG. 4B includes moving one bone portion relative to another bone portion to adjust an alignment of the bone portions relative to each other (452). In some examples, the distal portion of the transected first metatarsal 210 is rotated relative to the proximal portion of the transected metatarsal. The distal portion of the transected first metatarsal 210 may be rotated in the frontal plane and/or pivoted in the transverse plane and/or pivoted in the sagittal plane to help correct an anatomical misalignment of the distal portion of the metatarsal, as described herein.

After suitably moving the two transected bone portions relative to each other, the bone portions can be fixated to each other to secure and hold the new realigned position achieved through movement (452). The bone portions may or may not be provisionally fixated before being permanently fixated together. In either case, the portions can be permanently fixated using pins, plates, screws, staples or other fixation devices to provide stability during the healing process, as discussed above with respect to FIG. 4A and also discussed below with respect to FIGS. 9A-9C and 10.

Figure 4C:
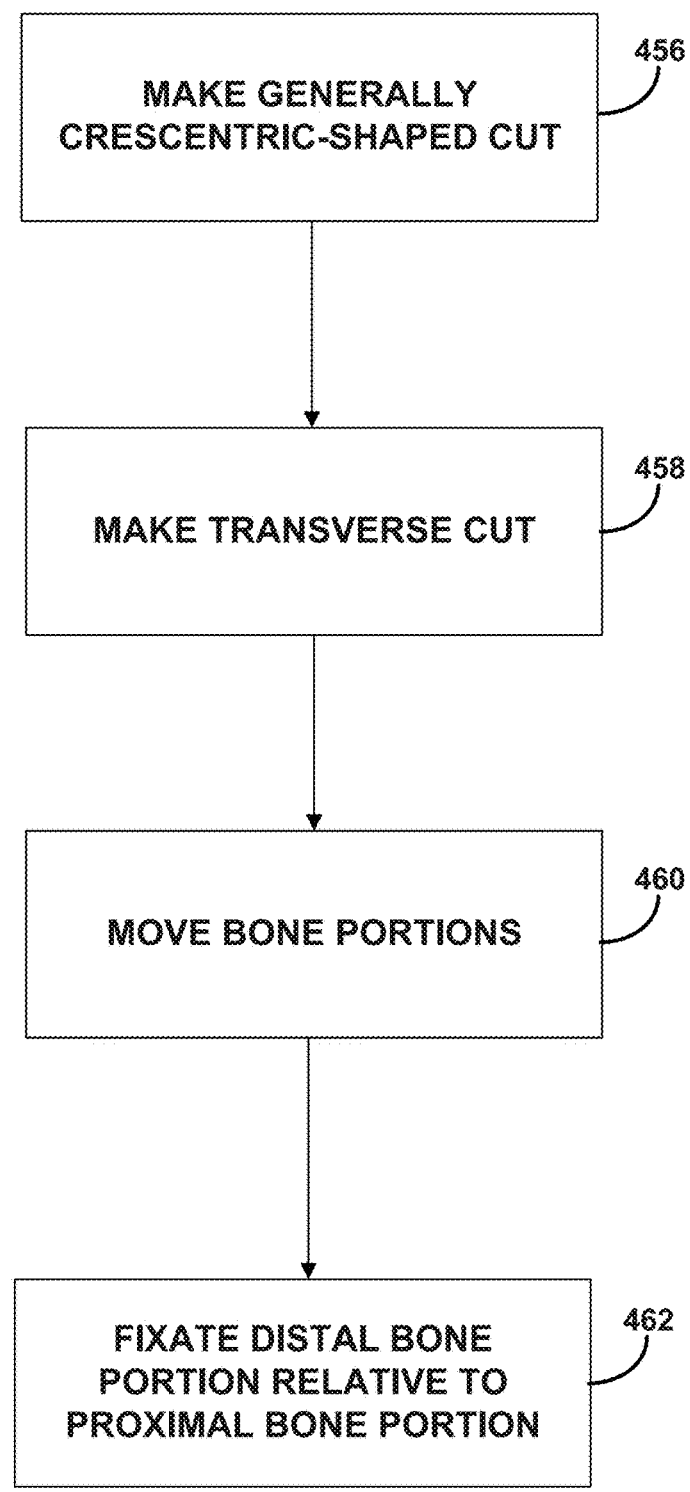

FIG. 4C is a flow diagram illustrating another example osteotomy technique for correcting an anatomical alignment. The example technique involves making a crescentic-shaped cut transecting metatarsal 210 (456). The cut separates the first metatarsal 210 into a proximal portion and a distal portion. One of the portions can have a concave-shaped end with a radius corresponding to the radius of the crescentic-shaped cut while the other portion can have a corresponding concave-shaped end of the same radius. In some examples, the proximal portion has the concave-shaped end and the distal portion has the convex-shaped end. The two portions may or may not be distracted to provide opposed ends separated from each other.

The technique of FIG. 4C further involves making a transverse, planar cut across the distal bone portion (458). The transverse, planar cut removes the concave- or convex-shaped end of the distal bone portion, forming a third or intermediate bone portion having the concave- or convex-shaped end previously defined by the distal bone portion. The ends of the distal bone portion and the intermediate bone portion facing each other may be planar.

After making the transverse, planar cut across, the technique further includes moving the distal metatarsal portion relative to the proximal metatarsal portion and/or the intermediate metatarsal portion to adjust an alignment of the distal and proximal bone portions relative to each other (460). In some examples, the distal portion of the transected first metatarsal 210 may be rotated in the frontal plane and/or pivoted in the transverse plane and/or pivoted in the sagittal plane to help correct an anatomical misalignment of the distal portion of the metatarsal. For example, the distal portion and the intermediate portion may each be moved in the transverse plane relative to the proximal portion, e.g., either the same distance or different distances. In some examples, the proximal ends of the distal portion and the intermediate portion are each translated medially in the transverse plane, e.g., causing the distal ends to pivot laterally to close the IMA.

In addition to or in lieu of translating the distal portion and the intermediate portion in the transverse plane, the distal portion may be rotated relative to the intermediate portion in the frontal plane. During movement, the planar proximal end face of the distal portion can rotate relative to the planar distal end face of the intermediate portion. In some examples, the distal portion is pivoted in the sagittal plane to also adjust the alignment of the distal portion in the sagittal plane.

After suitably moving the three transected bone portions relative to each other, the bone portions can be fixated to each other to secure and hold the new realigned position achieved through movement (462). The bone portions may or may not be provisionally fixated before being permanently fixated together. In either case, the portions can be permanently fixated using pins, plates, screws, staples or other fixation devices to provide stability during the healing process, as discussed above with respect to FIG. 4A and also discussed below with respect to FIGS. 9A-9C and 10.

Figure 4D:
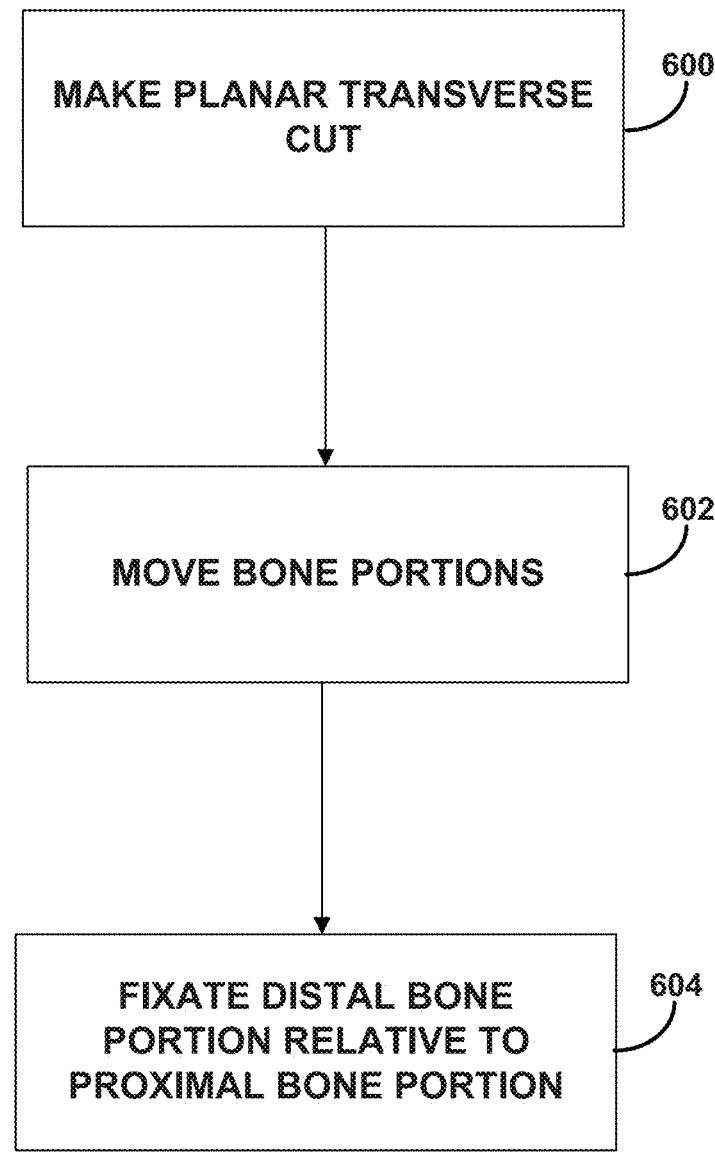

FIG. 4D is a flow diagram illustrating another example technique for correcting an anatomical alignment. The example technique involves making a planar cut transecting a metatarsal 210 (600). The planar cut separates the first metatarsal 210 into two portions: a proximal portion and a distal portion. Both bone portions may have planar cut end faces.

To make the planar cut, a planar cutting instrument such as a saw blade can be translated through the first metatarsal. The cutting instrument can be translated in any direction across the bone, including from the dorsal to the plantar side of the metatarsal or vice versa, or the medial to the lateral side of the metatarsal or vice versa. The cutting instrument can be translated through the first metatarsal parallel to the frontal plane or at a non-zero degree angle relative to the frontal plane. Likewise, the cutting instrument can be translated through the first metatarsal orthogonal to the transverse plane or at a non-zero degree angle relative to the transverse plane. Independent of the angle at which the planar cutting instrument is passed through the bone, the end faces formed by making the transecting cut according to FIG. 4D may be planar (e.g., non-curved).

After cutting the first metatarsal into two portions using a planar cutting instrument, the technique of FIG. 4D includes moving one bone portion relative to another bone portion in multiple planes to adjust an alignment of the bone portions relative to each other (602). In some examples, the distal portion of the transected first metatarsal 210 is rotated relative to the proximal portion of the transected metatarsal. The distal portion of the transected first metatarsal 210 may be rotated in the frontal plane and/or translated in the transverse plane and/or translated in the sagittal plane to help correct an anatomical misalignment of the distal portion of the metatarsal, as described herein.

After suitably moving the two transected bone portions relative to each other, the bone portions can be fixated to each other to secure and hold the new realigned position achieved through movement (604). The bone portions may or may not be provisionally fixated before being permanently fixated together. In either case, the portions can be permanently fixated using pins, plates, screws, staples or other fixation devices to provide stability during the healing process, as discussed above with respect to FIG. 4A and also discussed below with respect to FIGS. 9A-9C and 10.

Figures 5A, 5B:
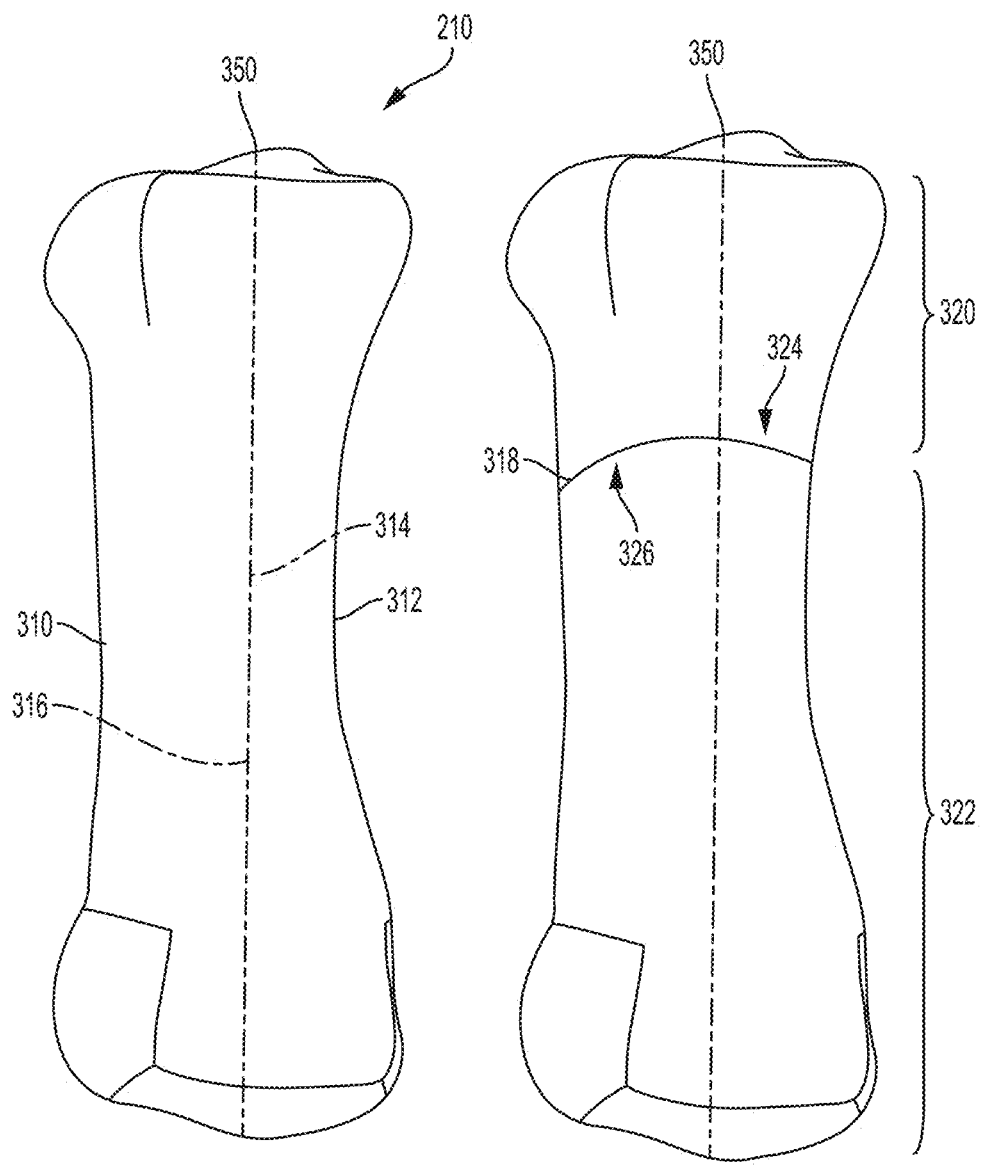
FIGS. 5A-5D show example procedural steps that can be performed to correct an anatomical misalignment of a bone.

FIGS. 5A-5D show example procedural steps that can be performed to correct an anatomical misalignment of a bone. As shown in FIG. 5A, the first metatarsal 210 is positioned in the transverse plane and defines a medial side 310, lateral side 312, dorsal side 314, and plantar side 316. To transect the first metatarsal 210, a first crescentic-shaped cut 318 can be made to form a proximal bone portion 320 and a distal bone portion 322. In different examples, the crescentic-shaped cut can make using a cutting instrument that makes a planar cut (e.g., planar blade, rotary cutter) that is translated through a curved arc or a curved-shaped cutting blade that is translated linearly to form the generally crescent-shaped cut. For example, the crescentic-shaped cutting blade may be translated parallel to the frontal plane of first metatarsal 210 (e.g., either from the dorsal to plantar side or plantar to dorsal side) to form the first crescentic-shaped cut 318.

In general, the terms crescent and crescentic are used interchangeably in this disclosure and refer to an arcuate shape having a uniform radius of curvature. The crescentic-shaped cut 318 defines new end faces separating the proximal portion 320 from the distal portion 322. In the illustration of FIG. 5B, the end face 324 of proximal portion 320 has a concave shape while the end face 326 of distal portion 322 has a corresponding convex shape. In other applications, the arc can be flipped so the end face 324 of proximal portion 320 has the convex shape while the end face 326 of distal portion 322 has the corresponding concave shape.

While the crescentic-shaped cut 318 can be made at any location along the length of first metatarsal 210, in some examples, the cut is made on the proximal portion of the metatarsal. For example, the crescentic-shaped cut 318 may be made on the proximal-most half of the first metatarsal 210, such as the proximal-most quarter, or proximal-most eighth of the first metatarsal. Positioning the crescentic-shaped cut 318 closer to the TMT joint may be useful to position the center of rotation, or Center of Rotational Angulation ("CORA"), formed between the proximal portion 320 and distal portion 322, farther back proximally along the length of foot 200 to approach a more anatomically correct alignment.

Figures 5C, 5D:
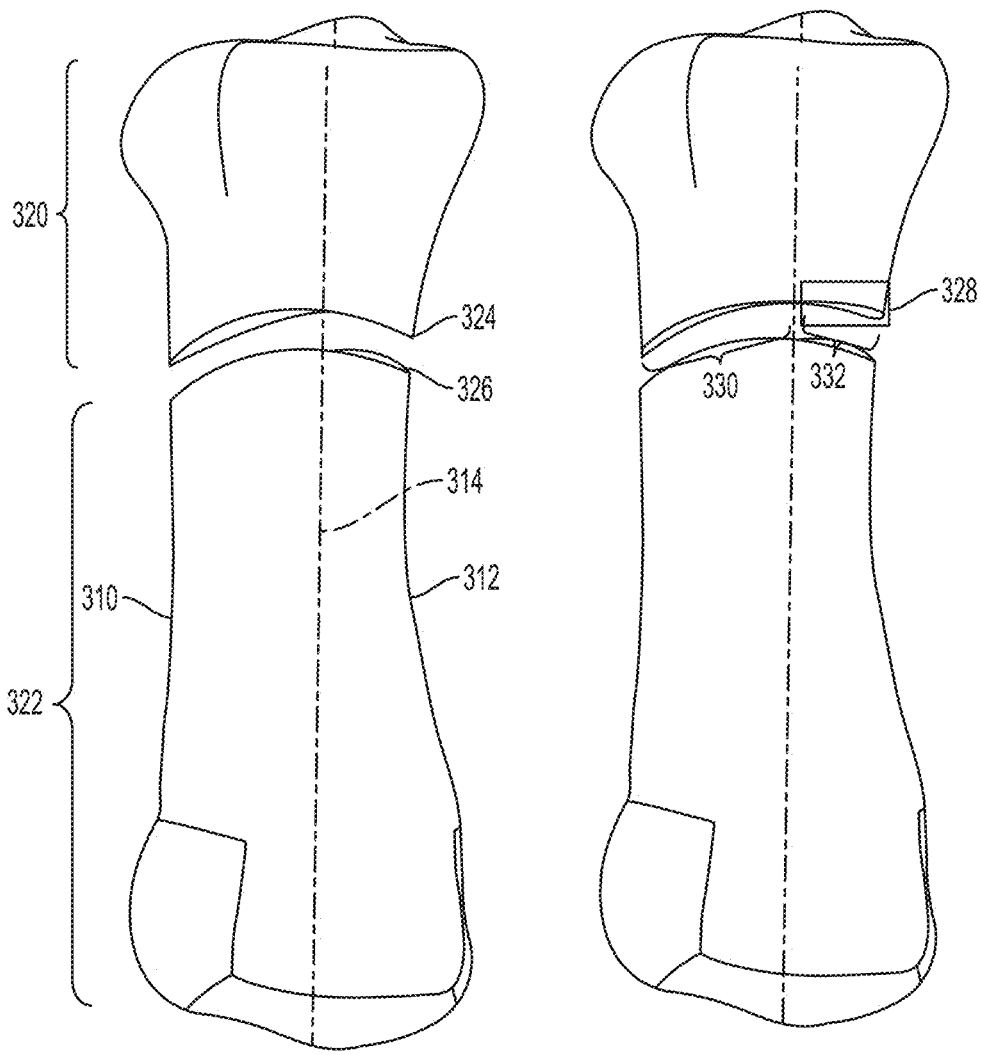

With reference to FIG. 5C, the distal portion 322 of the first metatarsal 210 can be distracted, or separated, from the proximal portion 320 of the metatarsal to expose the end faces of the respective bone portions. Thereafter, a second crescentic-shaped cut 328 can be made across the concave-shaped end face to create a second concavity 332 intersecting with a first concavity 330 formed by making the first crescentic-shaped cut 318. The second crescentic-shaped cut 328 may remove a section of bone to allow the end face of the distal bone portion 322 to be shifted in the medial direction 310 to realign the bone portion in one or more planes relative to proximal portion 320.

Figure 6:
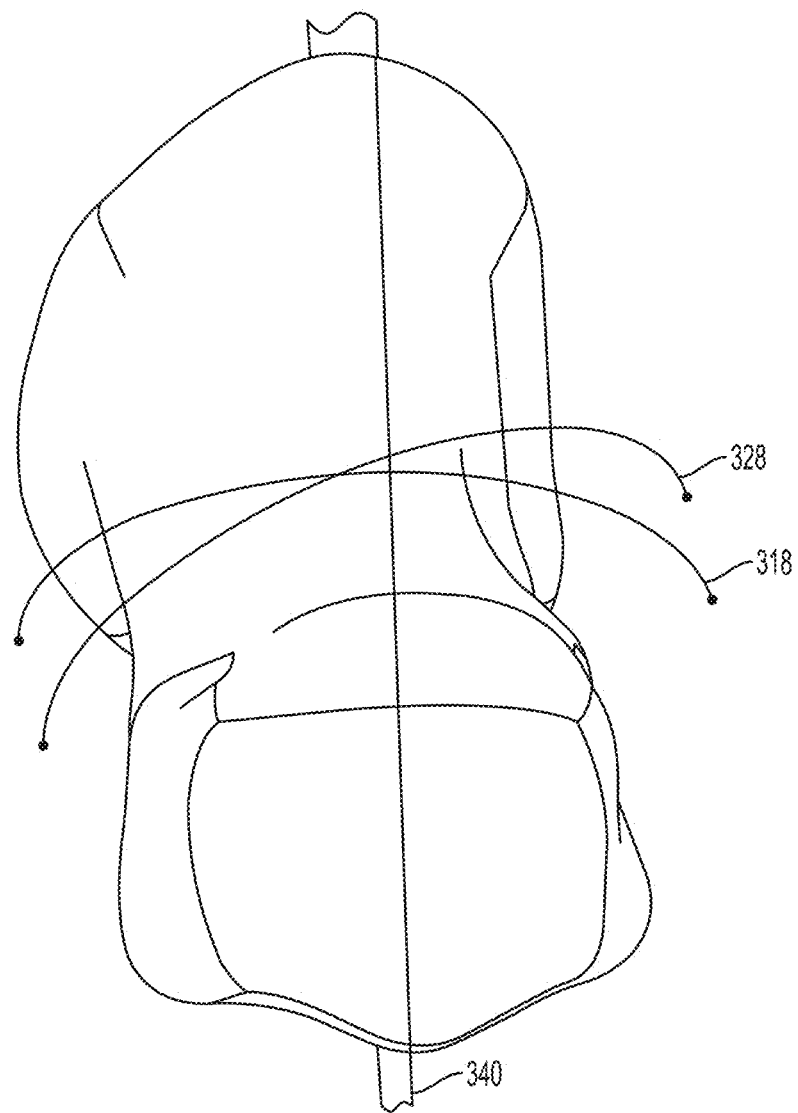
FIGS. 6 and 7 are perspective and frontal views, respectively, showing overlapping arcuate cuts that can be made to form first and second crescentic-shaped cuts, respectively.
Figure 7:
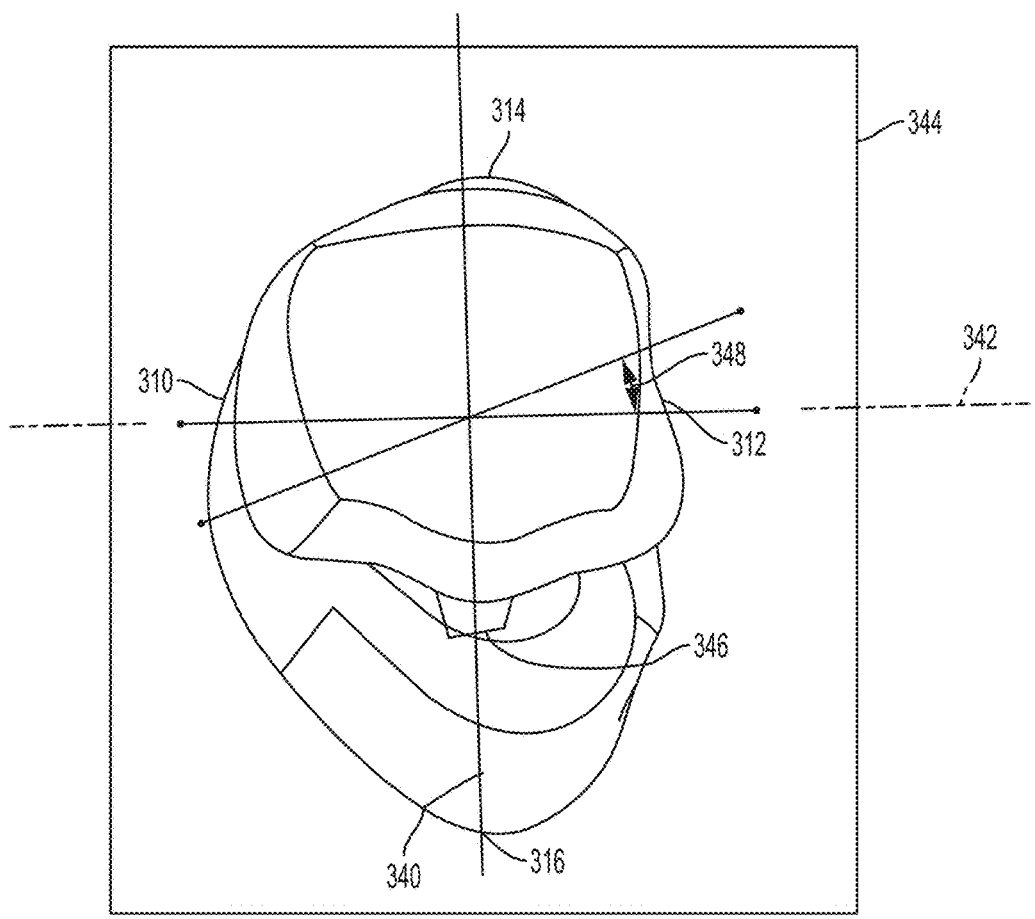

In some examples, the second crescentic-shaped cut 328 is formed by rotating the cutting instrument in the frontal plane relative to the position of the cutting instrument when making the first crescentic-shaped cut 318. Thereafter, the cutting instrument can be translated across the bone, e.g., causing the cutting instrument to form the second crescentic-shaped cut 328 at an angle relative to the angle at which the first crescentic-shaped cut 318 was made. FIGS. 6 and 7 are perspective and frontal views, respectively, showing overlapping arcuate cuts that can be made to form the first and second crescentic-shaped cuts 318 and 328, respectively. The arcuate cuts are shown overlapping on a unitary first metatarsal 210 for purposes of illustration although in practice, one of the cuts (either the first crescentic-shaped cut 318 or second crescentic-shaped cut 328) will be made to separate the metatarsal into two portions followed by the other of the two cuts.

In FIGS. 6 and 7, the first and second crescentic-shaped cuts 318 and 328 are made relative to a sagittal plane 340, a transverse plane 342, and a frontal plane 344. The sagittal plane 340 extends in the proximal to distal direction along the length of first metatarsal 210 and bisects metatarsal in the dorsal 314 to plantar 316 directions. The transverse plane 342 extends in the proximal to distal direction along the length of first metatarsal 210 and bisects metatarsal in medial 310 to lateral 312 directions. The frontal plane 344 transects the first metatarsal 210 at one particular location along the length of the metatarsal in the proximal to distal direction.

In the illustrated example, the first crescentic-shaped cut 318 is made parallel to the frontal plane 344, e.g., perpendicular to the transverse plane 342. However, the first crescentic-shaped cut 318 can be angled in the sagittal plane 340 (either in the proximal-to-distal direction or distal-to-proximal direction), such as an angle ranging from 2 degrees to 15 degrees relative to the frontal plane 344, such as from 5 degrees to 10 degrees relative to the frontal plane.

The second crescentic-shaped cut 328 may be made at an angle relative to the transverse plane 342. For example, the second crescentic-shaped cut 328 may be made at an acute angle 348 relative to the transverse plane. In some examples, the acute angle ranges from 10 degrees to 35 degrees, such as from 15 degrees to 25 degrees, or from 18 degrees to 23 degrees. The second crescentic-shaped cut 328 may be made in the same frontal plane as the frontal plane in which the first crescentic-shaped cut 318 is made or may be offset. For example, the second crescentic-shaped cut 328 may be at an angle ranging from 2 degrees to 15 degrees relative to the frontal plane 344, such as from 5 degrees to 10 degrees relative to the frontal plane.

Figure 8A:
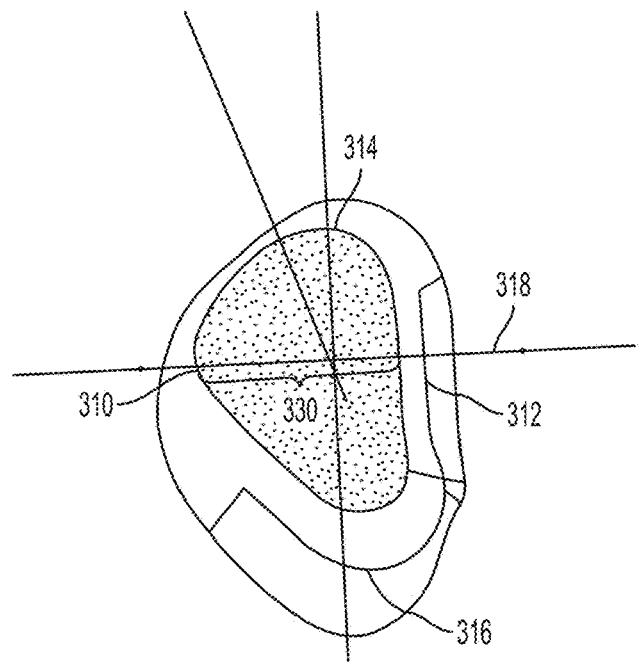
FIGS. 8A and 8B show frontal views of an example proximal bone portion at different stages of an example osteotomy technique.
Figure 8B:
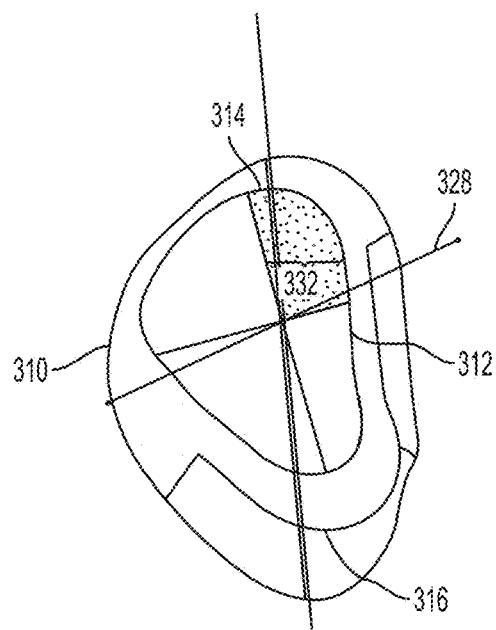

FIGS. 8A and 8B show frontal views of the proximal bone portion 320 at different stages of the example osteotomy technique. FIG. 8A illustrates the end face of proximal bone portion 320 after the first cut but prior to the second cut, resulting in the first concavity 330. The curvature of first crescentic-shaped cut 318 is illustrated in FIG. 8A overlaying the end face to show how the curvature has been formed by the generally crescent-shaped cut. FIG. 8B illustrates the end face of proximal bone portion 320 after the second cut, resulting in second concavity 332. The curvature of second crescentic-shaped cut 328 is illustrated in FIG. 8B overlaying the end face to show how the curvature has intersected with the curvature of the first cut. As shown in this example, a section of bone in a dorsal lateral quadrant of the end face has been removed by the second crescentic-shaped cut 328, thereby forming a second pocket or saddle (second concavity 332) that intersects with the main pocket or saddle (first concavity 330) formed by the first cut.

In practice, the same cutting instrument (e.g., having the same radius of curvature) used to form the first crescentic-shaped cut 318 may be used to form the second crescentic-shaped cut 328. Alternatively, a different sized and/or shaped cutting instrument may be used to form the second crescentic-shaped cut 328 from that used to form the first cut. In some examples, the cutting instrument used to form the first and/or second crescentic-shaped cuts 318, 328 has a radius of curvature ranging from 3 millimeters to 15 millimeters.

After forming the first and second crescentic-shaped cuts 318, 328, the clinician may move one bone portion (e.g., distal portion 322) relative to another bone portion (e.g., proximal portion 320) to realign that bone portion relative to the medial cuneiform 222 and/or an adjacent metatarsal, such as second metatarsal 212 (FIGS. 1A and 2A). For example, as discussed above with respect to FIG. 4A, the distal portion 322 of the transected first metatarsal 210 may be moved from an anatomically misaligned position relative to second metatarsal 212 and/or the medial cuneiform 222 to an anatomically aligned position. During movement, the end face of the distal portion 322 of the first metatarsal 210 created by making the first crescentic-shaped cut 318 can shift relative to the end face of the proximal portion 320 of the first metatarsal created by making the cut.

Figures 9A, 9B:
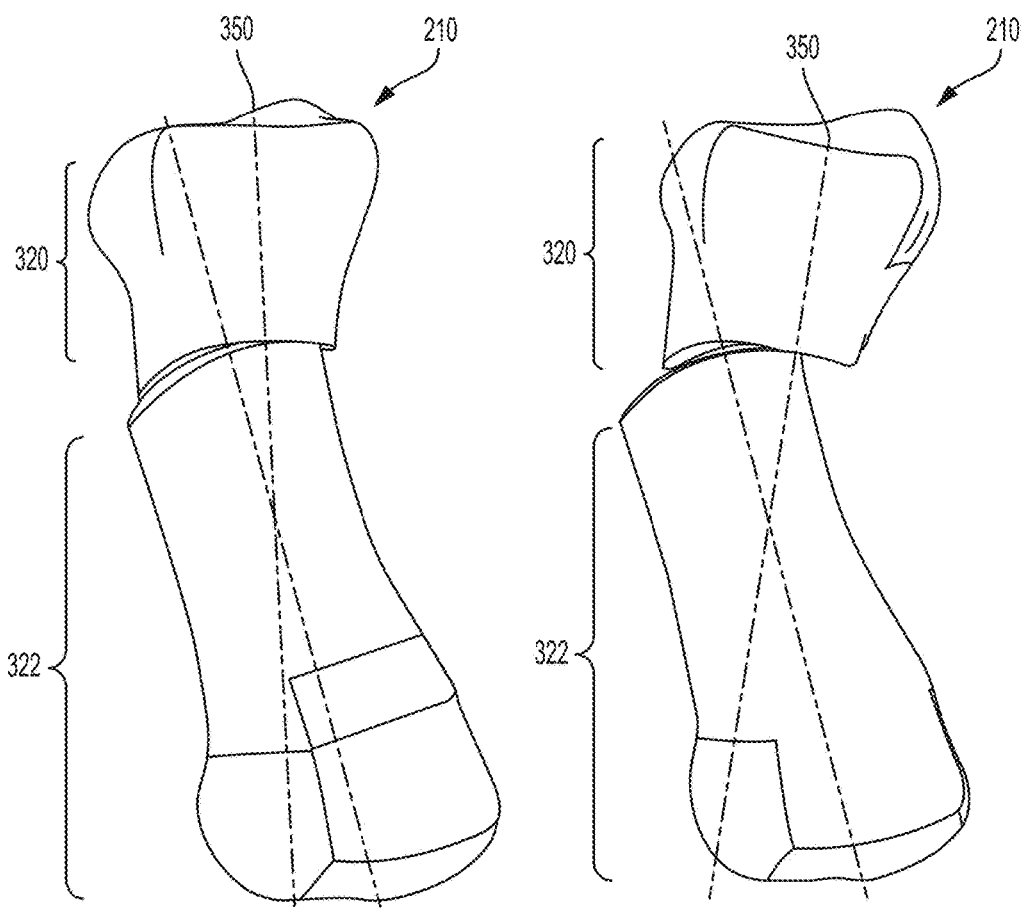
FIGS. 9A and 9B illustrate exemplary movement of a distal portion of a first metatarsal relative to a proximal portion.

In some examples, the lateral side of the end face of the distal portion 322 is repositioned in contact with a portion of end face of proximal portion 320 created by making the second crescentic-shaped cut 328. FIGS. 9A and 9B illustrate exemplary movement of a distal portion 322 relative to a proximal portion 320, e.g., to reduce the IMA in the transverse plane and/or reduce the extent of angular deformity in the frontal and/or sagittal planes. FIG. 9A illustrates example movement of distal portion 322 relative to proximal portion 320 to correct a comparatively minor deformity while FIG. 9B illustrates example movement for a more severe deformity.

To reposition the distal portion 322 relative to the proximal portion 320 in the example of FIGS. 9A and 9B, the distal portion 322 can be rotated in the frontal plane about an axis 350 extending parallel to the length of the metatarsal 210. Rotation of distal portion 322 about axis 350 can cause the proximal end of the distal portion to rotate into the second saddle or concavity 332 (illustrated on FIG. 8B) formed by making the second crescentic-shaped cut 328. In some examples, the distal portion 322 is rotated relative to the proximal portion 320 until the sagittal plane 340 bisects the crista prominence 346 on the plantar side of the foot, as illustrated in FIG. 7. Additionally or alternatively, the distal portion 322 can be pivoted in the transverse plane (e.g., such that the distal end of the distal portion is translated from the medial to lateral direction) to close the IMA. Further additionally or alternatively, the distal portion 322 may be pivoted in the sagittal plane (e.g., such that the distal end of the distal portion is translated plantarly or dorsally) to correct a sagittal plane misalignment.

In some applications, the distal portion 322 is moved in multiple planes (2 or 3 planes) relative to the proximal portion 320 to move the distal portion from an anatomically misaligned position to an anatomically aligned position. With respect to the frontal plane, a normal first metatarsal will be positioned such that its crista prominence 346 (FIG. 7) is generally perpendicular to the ground (e.g., bisected by the sagittal plane) and/or its sesamoid bones are generally parallel to the ground and positioned under the metatarsal. This position can be defined as a metatarsal rotation of 0 degrees. In a misaligned first metatarsal, the metatarsal may be axially rotated between about 4 degrees to about 30 degrees or more. Accordingly, in some applications, the distal portion 322 is moved relative to the proximal portion 320 to anatomically align the distal portion by reducing the metatarsal rotation in the frontal plane from about 4 degrees or more to less than 4 degrees (e.g., to about 0 to 2 degrees) by rotating the distal portion 322 with respect to the proximal portion 320.

Figure 9C:
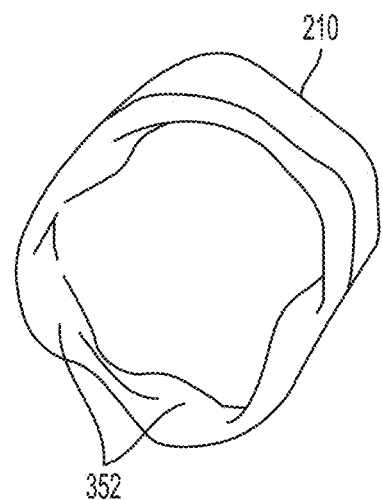
FIGS. 9C and 9D are frontal plane views showing examples sesamoid bone positions before and after an example anatomical realignment, respectively.
Figure 9D:
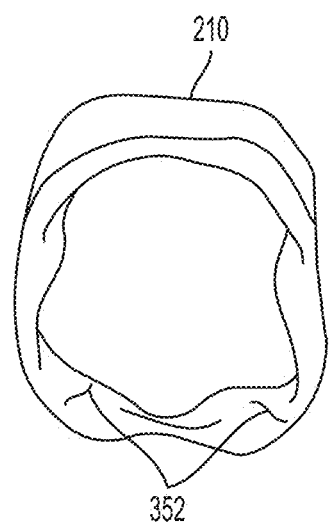

In an anatomically misaligned metatarsal, the hallux sesamoid bones in the foot of the patient may be rotated relative to their normal, anatomically-aligned position. The hallux sesamoids are two ovoid-shaped ossicles within the flexor hallucis brevis muscles where the muscles pass over the metatarsophalangeal joint (joint 232 in FIG. 2A) between the first metatarsal 210 and proximal phalanx 220. FIG. 9C is a frontal plane view of first metatarsal 210 showing an example frontal plane rotational misalignment of the sesamoid bones 352. In some examples, the distal portion 322 is rotated in the frontal plane until the sesamoids 352 are generally parallel to the ground and positioned under the metatarsal, e.g., bisected by the sagittal plane. Repositioning of the sesamoids after an example rotational realignment in the frontal plane is illustrated in FIG. 9D. Additional details on rotation correction techniques for bone portions that can be used in accordance with the disclosure are described in U.S. patent application Ser. No. 14/981,335, entitled "BONE POSITIONING AND PREPARING GUIDE SYSTEMS AND METHODS" and filed on Dec. 28, 2015, the entire contents of which are incorporated herein by reference.

In some examples, a clinician performing an anatomical realignment according to the disclosure (for example, using one or more of the cutting techniques described with respect to FIGS. 4A-4D), may use imaging equipment within the operating suit to help visualize and guide the realignment process. For example, the clinician may use fluoroscopy to visualize the positioning of bones during one or more portions of the realignment technique, such as during cutting and/or while realigning a distal bone portion relative to a proximal bone portion. To aid visualization and/or movement of one bone portion relative to another bone portion, the clinician may insert one or more pins (e.g., metal rods) into the bone before or after making a transecting cut.

In some examples, the clinician inserts a pin into the distal portion of the bone before making a transecting cut (e.g., using a planar, crescentic, spherical, or other shaped cutting instrument). Additionally or alternatively, the clinician may insert a pin into the proximal portion of the bone before making the transecting cut. As alternatives, one or both pins may be inserted after making the transecting cut, although it may be procedurally simpler to insert the pin(s) before making the cut. The clinician may insert the pin in the distal portion so the tip of the pin is inserted at an angle in the lateral-plantar direction into the bone. This may result in the head of the pin projecting out of the bone in the medial-dorsal quadrant. Other insertion directions can be used.

After making the transecting cut, the clinician may use the pin as a guiding instrument to facilitate movement of the distal bone portion relative to the proximal bone portion. For example, the clinician may apply a translating force and/or a rotary force to the pin, optionally while observing the amount of movement under fluoroscopic imaging, to guide the distal bone portion to a suitably realigned position. The clinician may use the anatomical standards and/or landmarks described above to determine when the distal bone portion has been suitably realigned. In some examples, the distal bone portion is rotated until the sesamoid bones on the distal portion are centered plantarly. Example anatomical landmarks are described below with respect to FIGS. 18A and 18B.

After suitably moving the distal and proximal bone portions 322, 320 relative to each other, the bone portions may be fixated to provide a stable orientation during healing. In some examples, the distal and proximal bone portions 322, 320 are provisionally fixated relative to each other before permanently fixating the bone portions relative to each other. Provisional fixation can temporarily hold the proximal bone portion 320 and distal bone portion 322 in fixed alignment relative to each other while one or more permanent fixation devices are applied to the bones and across the joint formed therebetween. To provisionally fixate the bone portions relative to each other, a fixation wire may be driven in the proximal bone portion 320 and distal bone portion 322. Additionally, or alternatively, a compression pin, such as a threaded olive pin, may be inserted through the proximal portion 320 and into the distal portion 322, or vice versa, to provide compression and provisional fixation between the two bone portions.

Figure 10:
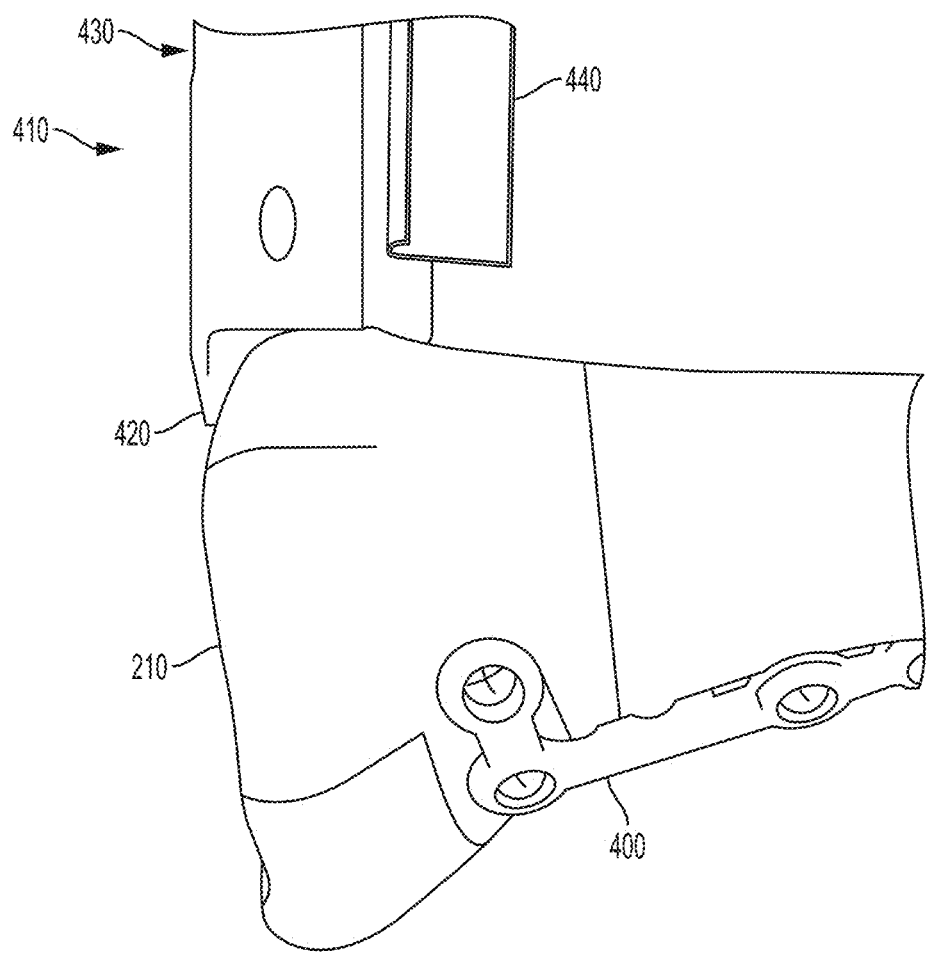
FIG. 10 illustrates an example bone plate and example cutting guide that may be used to perform an osteotomy technique according to the disclosure

Independent of whether the proximal bone portion 320 and distal bone portion 322 are provisionally fixated together, the clinician may apply a permanent fixation device to the bone portions and across the joint between the bone portions. The permanent fixation device can hold the bone portions in fixed alignment relative to each other, e.g., to promote healing between the bone portions in their aligned positions. In different examples, one or more bone plates, pins, screws, staples, or other fixation mechanisms can be used to fixate the bones relative to each other. FIG. 10 illustrates an example configuration of a bone plate 400 that may be used to bridge the joint formed between the proximal portion and the distal portion of the first metatarsal.

When using a bone plate, a variety of different shaped bone plates can be used, including helical-shaped bone plates, T-shaped bone plates, and L-shaped bone plates.

Additionally, while different cutting hardware can be used to execute an osteotomy technique according to the disclosure, FIG. 10 illustrates one example cutting guide 410 that may be useful to perform the technique. As shown, cutting guide 410 includes a seeker portion 420 projecting plantarly from a main body 430. The seeker portion may be configured (e.g., sized and/or shaped) to be inserted in a TMT joint between first metatarsal 210 and medial cuneiform 222, thereby providing a comparatively stable and fixed platform from which to guide cutting. The main body 430 of cutting guide 410 extends distally along first metatarsal 210 and may define a guide surface along with a cutting instrument can be translated to perform one or more cuts as described herein.

Figures 11A, 11B:
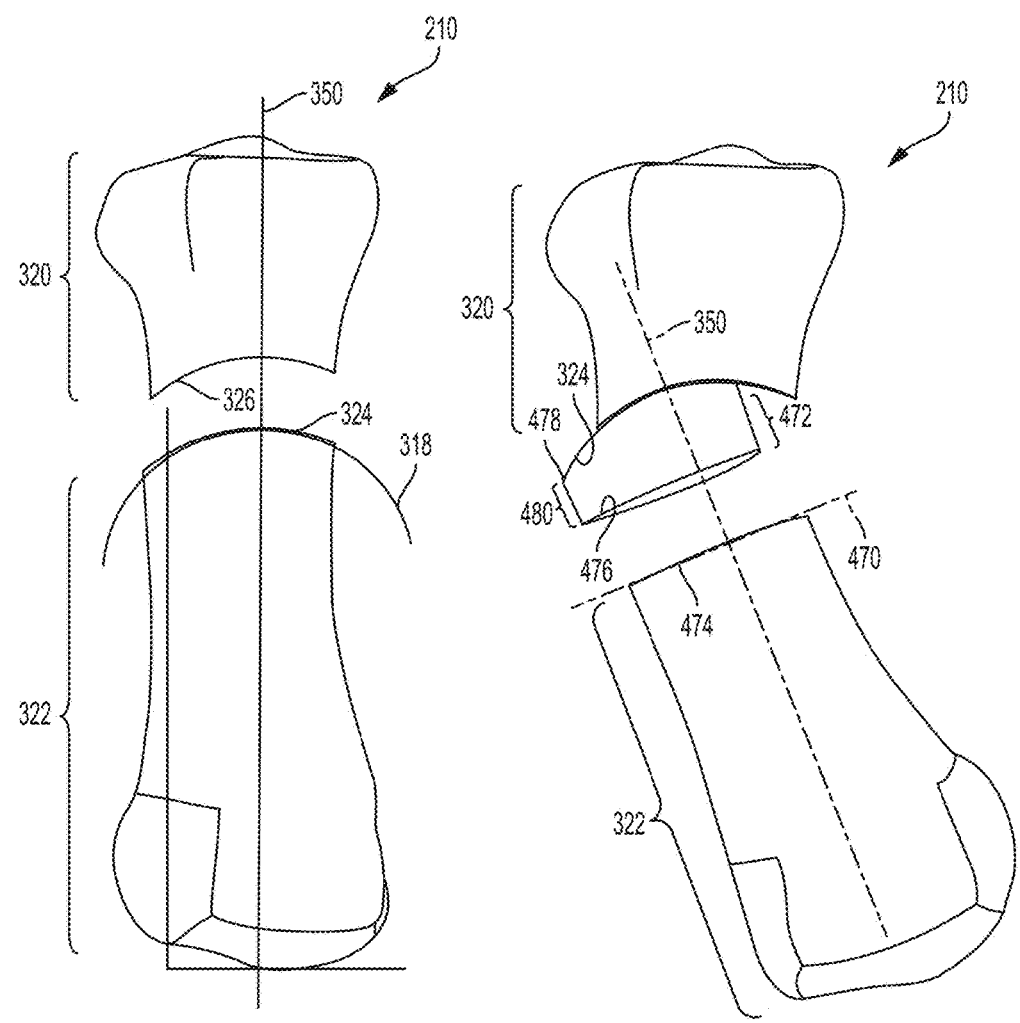
FIGS. 11A-11C show example procedural steps that can be performed to correct an anatomical misalignment of a bone using a combination of crescentic-shaped and planar cuts.
Figure 11C:
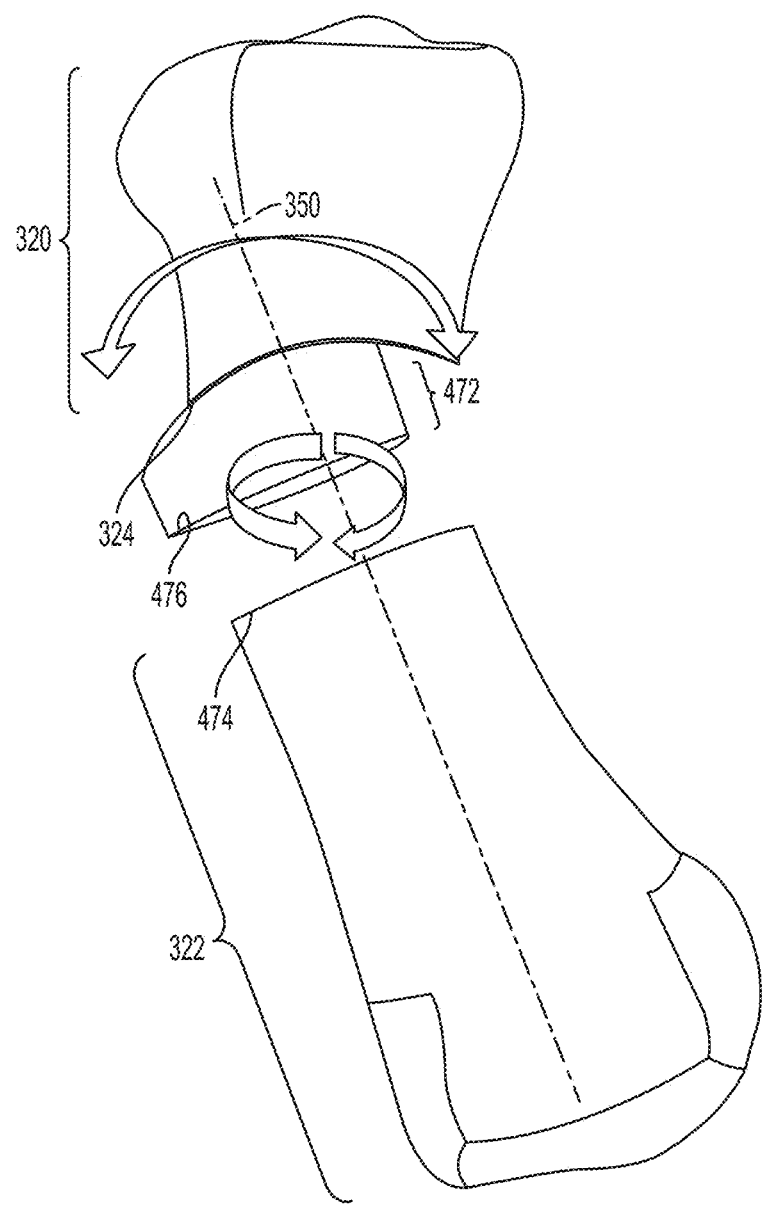

As yet another example, an osteotomy correction technique may be performed using a combination of a crescentic-shaped cut and a planar (e.g., non-curved) cut. FIGS. 11A-11C show example procedural steps that can be performed to correct an anatomical misalignment of a bone using a combination of crescentic-shaped and planar cuts. As shown in FIG. 11A, the first metatarsal 210 can be transected by making a crescentic-shaped cut 318 to form a proximal bone portion 320 and a distal bone portion 322, as discussed above with respect to FIGS. 5A-5D. In different examples, the crescentic-shaped cut 318 can be made using a cutting instrument that makes a planar cut (e.g., planar blade, rotary cutter) that is translated through a curved arc or a curved-shaped cutting blade that is translated linearly to form the generally crescent-shaped cut. In some examples, the crescentic-shaped cut 318 is made so the end face 324 of proximal portion 320 has a concave shape while the end face 326 of distal portion 322 has a corresponding convex shape.

With reference to FIG. 11B, a planar cut 470 can be made across the distal portion 322 to form an intermediate bone portion 472. The planar cut 470 can be made prior to making the crescentic-shaped cut 318 or after making the crescentic-shaped cut. In either case, the planar cut 470 can form a new planar end face 474 on the proximal end of the distal portion 322. This can cause the crescentic-shaped end face 324 previously defined by the distal portion 322 to become the proximal end face of the newly formed intermediate portion 472. The distal end face 476 of the intermediate portion 472 may be planar, corresponding to the planar end face 474 on the distal portion 322.

The planar cut 470 can be made by translating a cutting instrument through the distal portion 322. The planar cut 470 may be offset from the crescentic-shaped end face 324 formed by making the crescentic-shaped cut 318 (or that will be formed upon subsequently making the crescentic-shaped cut in instances where the planar cut is made first). In some examples, the planar cut 470 is offset from the terminal edge 478 of the crescentic-shaped end face 324 a distance 480 ranging from 2 to 30 millimeters, such as from 7 to 25 millimeters.

In the illustrated example, the planar cut 470 is made parallel to the frontal plane, e.g., perpendicular to the transverse plane. However, the planar cut can be angled in the sagittal plane (either in the proximal-to-distal direction or distal-to-proximal direction), such as an angle ranging from 2 degrees to 15 degrees relative to the frontal plane 344, such as from 5 degrees to 10 degrees relative to the frontal plane.

To adjust the anatomical alignment of the distal portion 322 relative to the proximal portion 320 and/or intermediate portion 472, the distal portion can be moved. In some examples as illustrated in FIG. 11C, the distal portion 322 and intermediate portion 472 are translated in the transverse plane. The distal portion 322 and intermediate portion 472 can be pivoted in the transverse plane (e.g., such that the distal end of the distal portion is translated from the medial to lateral direction) to close the IMA. As the distal portion 322 and intermediate portion 472 are pivoted, the crescentic-shaped end face 324 of the intermediate portion can translate along the arc of the corresponding crescentic-shaped end face 326 of the proximal portion. The planar end faces 474 and 476 of the intermediate and distal portions may not move relative to each other during this pivoting movement.

Additionally or alternatively, the distal portion 322 can be rotated in the frontal plane about an axis 350 extending parallel to the length of the metatarsal 210. Rotation of distal portion 322 about axis 350 can cause the planar end face 474 on the proximal end of the distal portion 322 to rotate relative to the planar end face 476 on the intermediate portion, which may remain rotationally stationary during movement. In some examples, the distal portion 322 is rotated relative to the intermediate portion 472 and proximal portion 320 until the sagittal plane 340 bisects the crista prominence 346 on the plantar side of the foot, as illustrated in FIG. 7. Further additionally or alternatively, the distal portion 322 may be pivoted in the sagittal plane (e.g., such that the distal end of the distal portion is translated plantarly or dorsally) to correct a sagittal plane misalignment. The distal portion 322 can be moved relative to the intermediate bone portion 472 and/or proximal bone portion 320 to achieve any of the anatomical alignment positions described herein.

After suitably moving the distal bone portion 322, proximal bone portion 320, and intermediate bone portion 472 relative to each other, the bone portions may be fixated to provide a stable orientation during healing. In some examples, the distal, intermediate, and proximal bone portions 322, 472, 320 are provisionally fixated relative to each other before permanently fixating the bone portions relative to each other. In either case, a clinician may apply a permanent fixation device to the three bone portions and across the two joints between the three bone portions. In different examples, one or more bone plates, pins, screws, staples, or other fixation mechanisms can be used to fixate the bones relative to each other.

Figure 12:
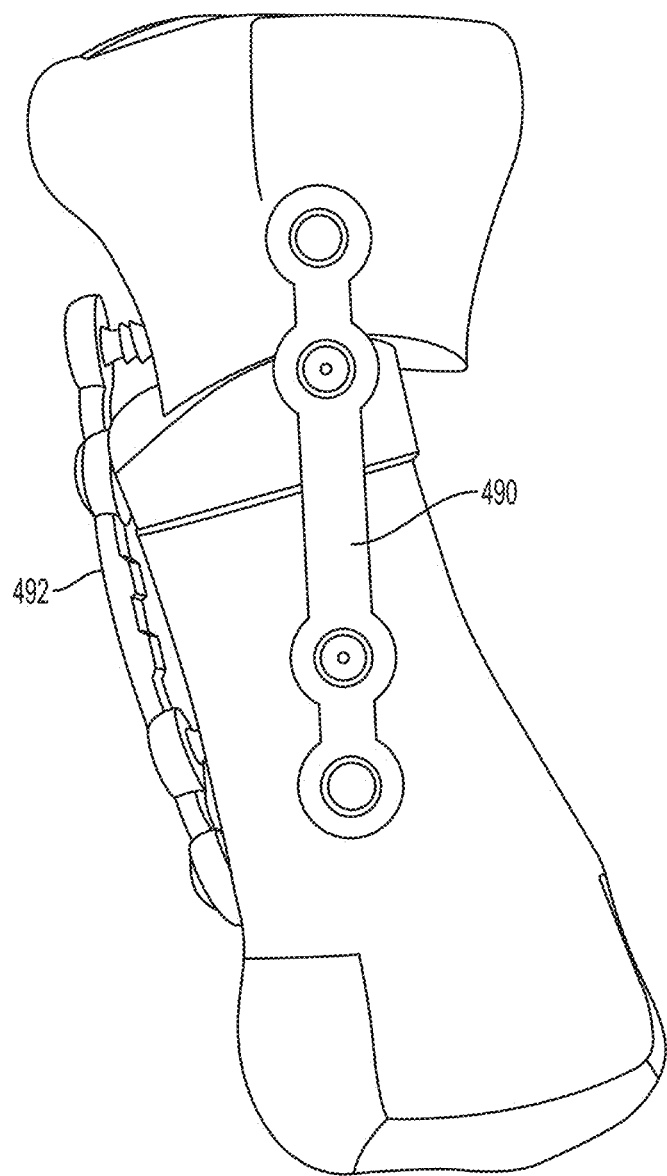
FIG. 12 illustrates an example fixation arrangement that includes a first bone plate and a second bone plate.

FIG. 12 illustrates an example fixation arrangement that includes a first bone plate 490 and a second bone plate 492. The bone plates bridge the joint formed between the distal portion and the intermediate portion as well as the joint formed between the intermediate portion and the proximal portion. In some examples, a bone plate is secured on the dorsal-medial side of the distal, intermediate, and proximal bone portions across the joints formed by transecting the first metatarsal 210 into the three bone portions. Additionally or alternatively, a bone plate may be secured on a different portion of the bones.

While the foregoing discussion has generally described osteotomy techniques involving multiple crescentic-shaped cuts, it should be appreciated that the techniques may be performed without making multiple crescentic-shaped cuts in other applications. For example, in instances where a generally spherical-shaped cutting instrument is used, a single cut may be made to transect the first metatarsal 210 and define the ends of the respective bone portions.

Figure 13:
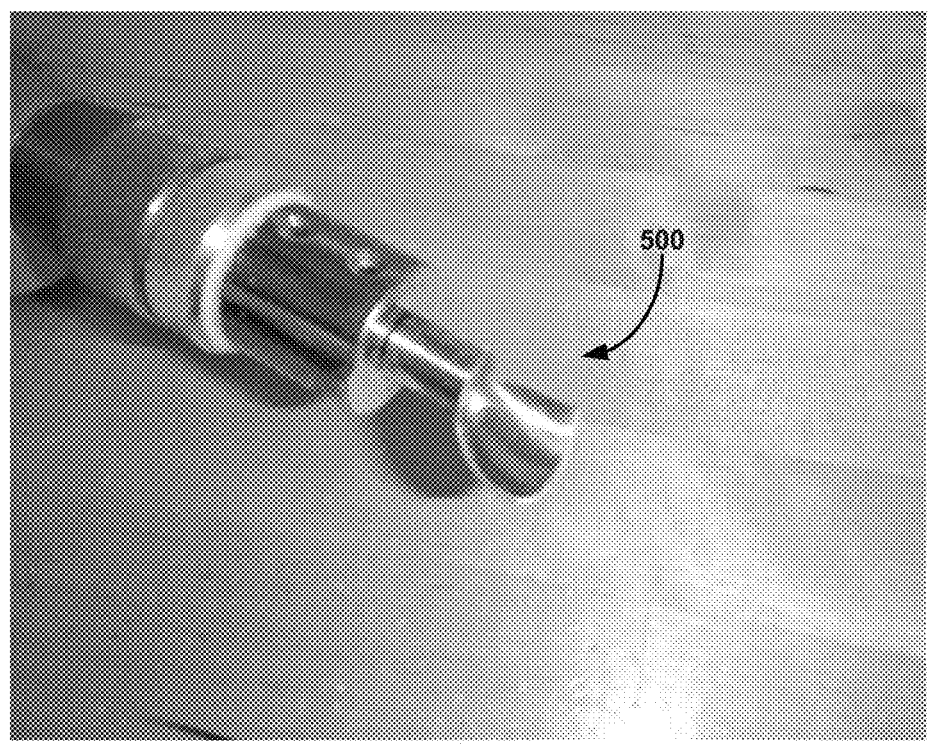
FIG. 13 is an illustration of an example generally spherical-shaped cutting blade that can be used to transect a metatarsal during a bone realignment procedure.

FIG. 13 is an illustration of an example generally spherical-shaped cutting blade 500 that can be used to transect a metatarsal during a bone realignment procedure. In use, the generally spherical-shaped cutting blade 500 may be translated through an arc tracing the surface of an imaginary sphere to form the generally spherical-shaped cut. The cutting blade can form one metatarsal portion having a generally spherical-shaped projection and an opposed metatarsal portion having a generally spherical-shaped recess. When used, the generally spherical-shaped cutting blade 500 can have a diameter ranging from 6 millimeters to 30 millimeters, although cutting blades of other dimensions can also be used.

Figure 14A:
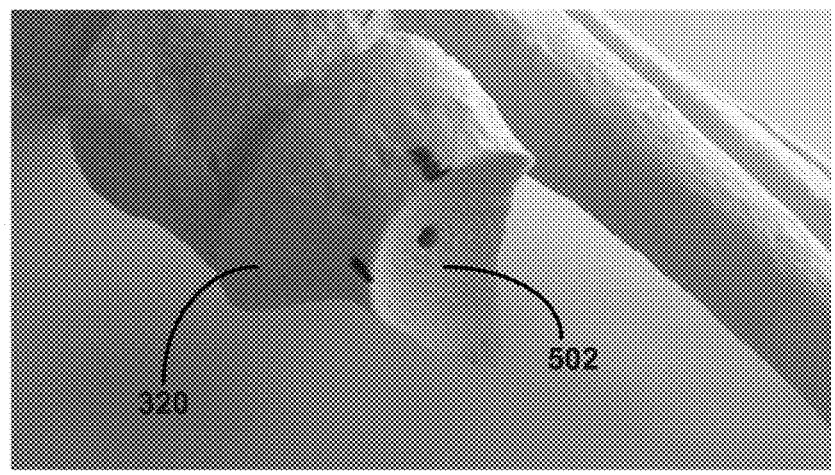
FIGS. 14A and 14B are illustrations of example end faces formed by transecting a first metatarsal with a generally spherical-shaped cutting blade.
Figure 14B:
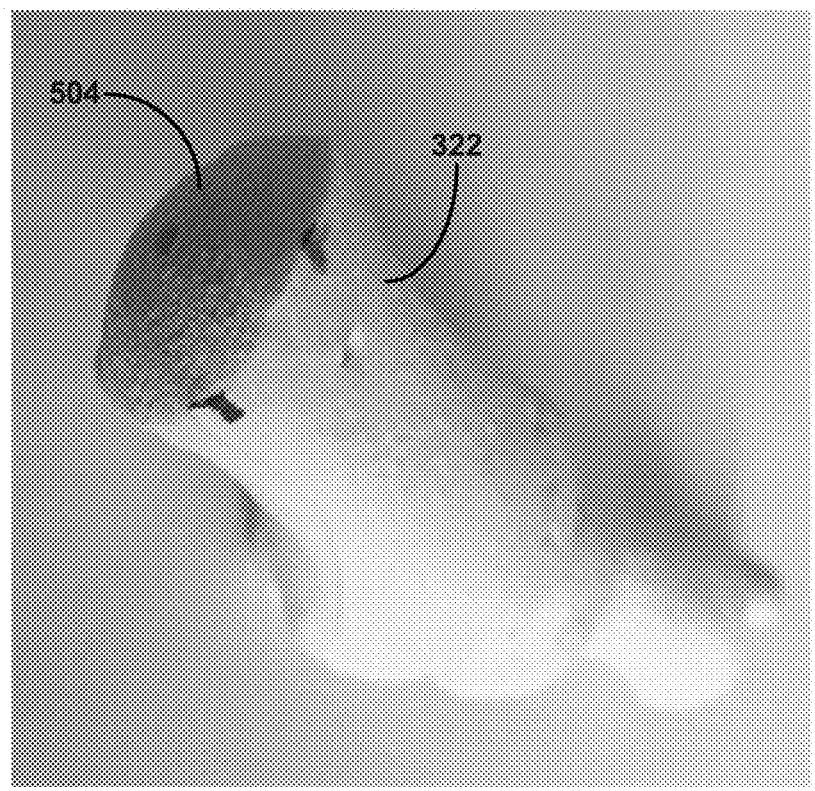

FIGS. 14A and 14B are illustrations of example end faces formed by transecting a first metatarsal with generally spherical-shaped cutting blade 500. FIG. 14A illustrates an example proximal portion 320 having a concave or socket end face 502. FIG. 14B illustrates an example distal portion 322 having a convex or ball end face 504. The end faces illustrated in FIGS. 14A and 14B can be created be positioning the CORA of the generally spherical-shaped cutting blade 500 over the first metatarsal and thereafter translating the blade through the bone, e.g., from a medial to lateral direction or vice versa. In other applications, the generally spherical-shaped cutting blade 500 may be positioned such that the proximal portion 320 resulting after the cut has the convex or ball end face while the distal portion 322 has the concave or socket end face. This reverse orientation can be achieved by positioning the CORA of the generally spherical-shaped cutting blade 500 over the medial cuneiform and thereafter translating the blade through the first metatarsal, e.g., from a medial to lateral direction or vice versa. In yet other applications, the CORA of the generally spherical-shaped cutting blade 500 can be positioned over either the first metatarsal or the medial cuneiform and the blade translated through the first metatarsal from a dorsal to a plantar direction.

Figure 15B:
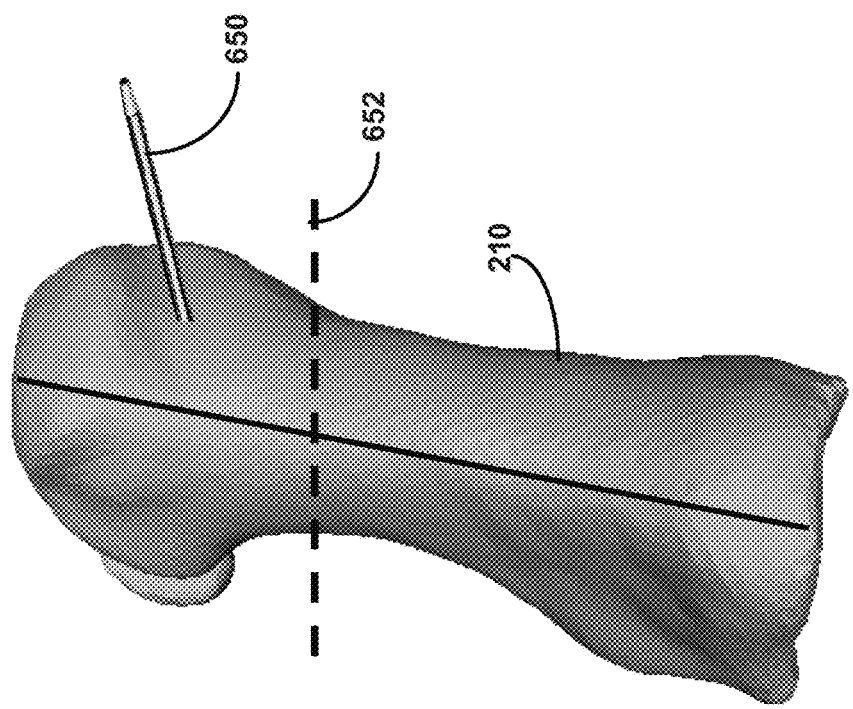
FIGS. 15A-15D illustrate example osteotomy procedure steps that may be performed to realign a bone or bone portion using a planar cutting instrument according to the technique of FIG. 4D.
Figure 15A:
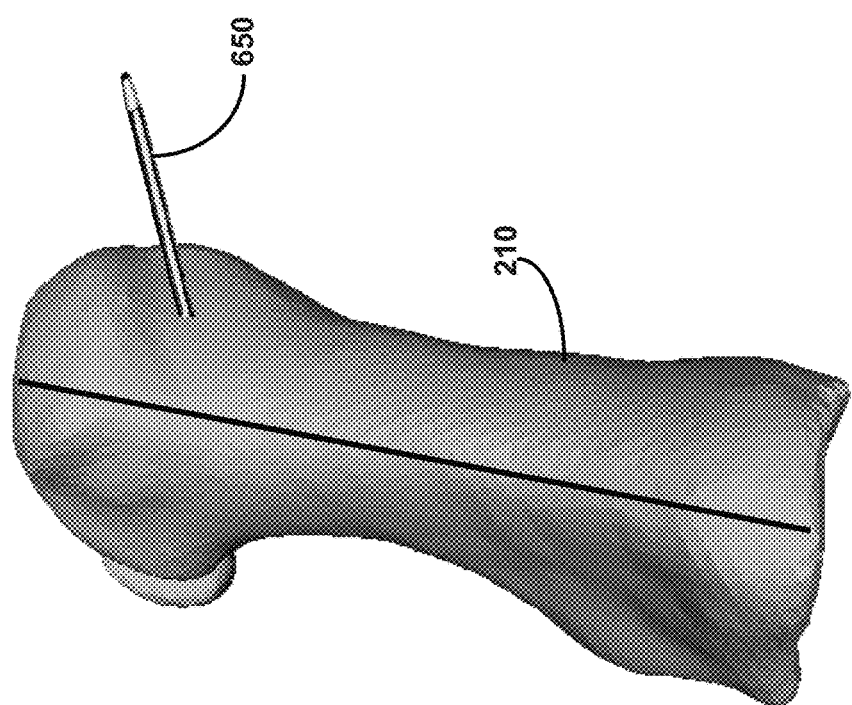
Figure 15D:
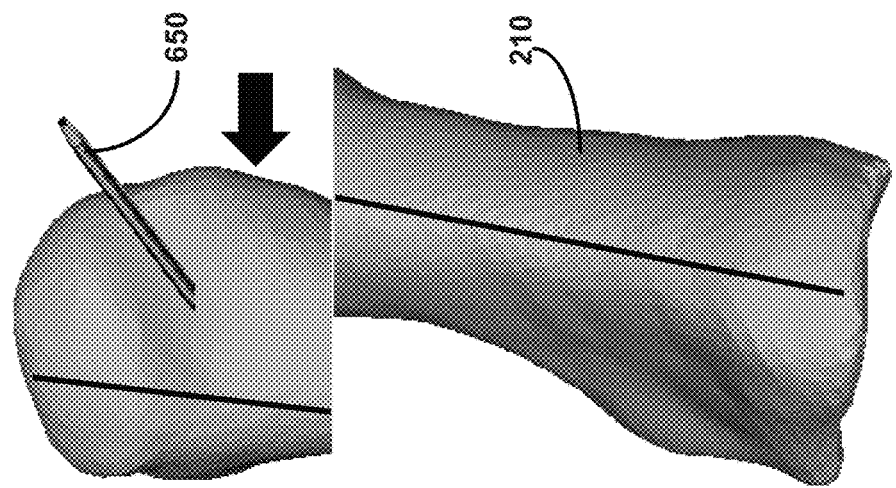
Figure 15C:
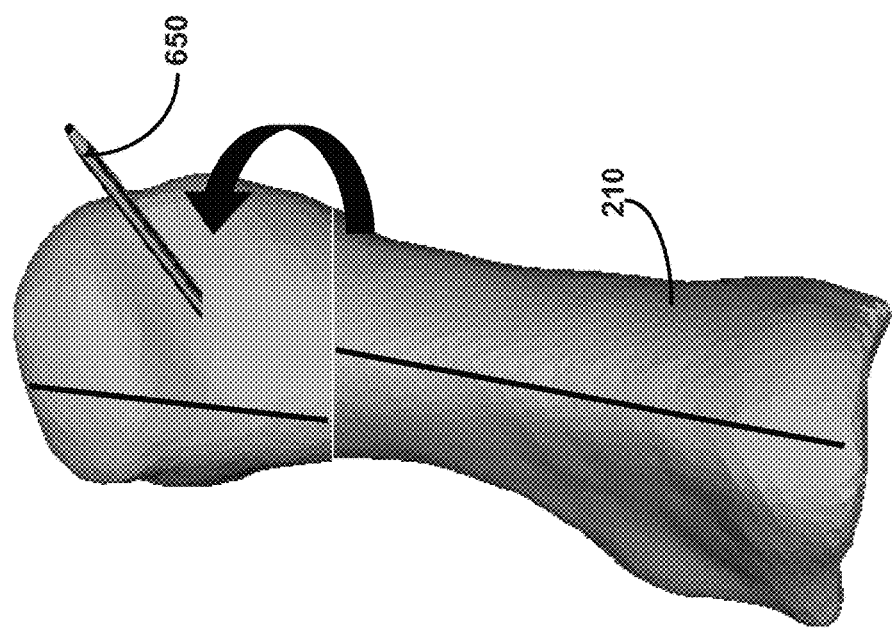

FIGS. 15A-15D illustrate example osteotomy procedure steps that may be performed to realign a bone or bone portion using a planar cutting instrument according to the technique of FIG. 4D. FIG. 15A is a dorsal to plantar view of a first metatarsal 210 with an example frontal-plane rotation and transverse-plane medial deviation, resulting in an increased IM angle. A guide pin 650 has been inserted in the distal head of the metatarsal in preparation for further surgical procedure steps. FIG. 15B illustrates an example planar osteotomy cut line 652 though which a planar cutting instrument is passed to transect the metatarsal 210 into a distal portion and a proximal portion. FIG. 15C illustrates an example frontal-plane rotational correction that can be applied to the distal bone portion. The clinician may grasp the guide pin 650 and use the guide pin to correct the rotation of the distal metatarsal segment in the frontal-plane. In some examples, the clinician visualizes the rotational realignment and use the rotational position of guide pin 650 to visually guide the degree of rotational correction applied to the distal metatarsal portion. In addition, FIG. 15D illustrates an example lateral translation that can be applied to the distal bone portion, either before, after, or concurrent with rotating the distal bone portion in the frontal plane (FIG. 15C). The distal bone portion can be translated laterally in the transverse plane to address the transverse-plane medial deviation of the metatarsal, helping to reduce or eliminate the bunion "bump". Although not illustrated, the distal bone portion can be translated in the sagittal plane in addition to or in lieu of translating the bone portion in the transverse plane.

The clinician may visually monitor the position of guide pin 650 and use the position of the pin (e.g., the angle of rotation of the pin) to determine when the distal bone portion is adequately realigned. Additionally, or alternatively, the clinician may view the position of guide pin 650 and/or the position of one or more anatomical landmarks on the distal bone portion under fluoroscopy to determine when the distal bone portion is adequately realigned. Once suitably realigned, the clinician may provisionally and/or permanently fixate the realigned distal bone portion to the proximal bone portion, as discussed above.

Figure 16B:
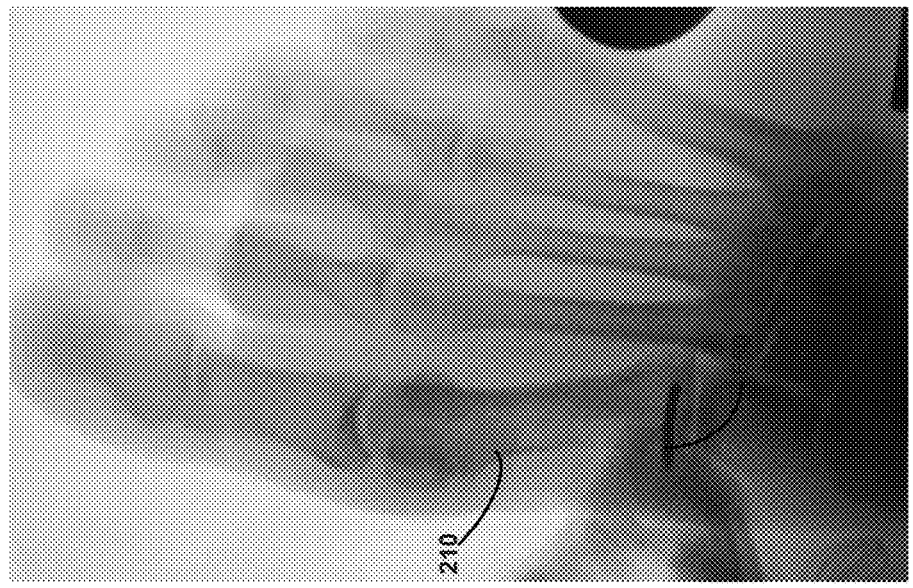
FIGS. 16A and 16B are example images showing how a guide pin can be used during to help facilitate realignment of one bone portion relative to another bone portion.
Figure 16A:
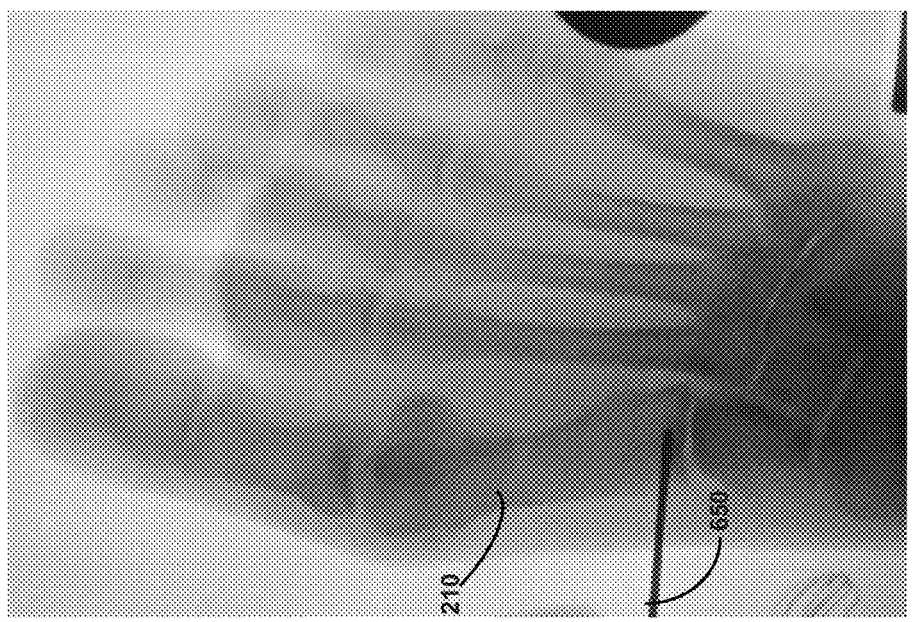

FIGS. 16A and 16B are example images showing how a guide pin can be used to help facilitate realignment of one bone portion relative to another bone portion. FIG. 16A illustrates a first metatarsal 210 having frontal-plane rotation deviation. A guide pin 650 is inserted into the metatarsal. The rotational position of guide pin 650 can be used by the clinician to help visually determine (e.g., with the unaided eye or under fluoroscopic imaging) when the portion of the first metatarsal being rotationally realigned has been suitably rotated in the frontal plane. In some examples, the clinician also uses guide pin 650 as a grasping instrument to manually grasp the pin and rotate the bone portion being realigned. FIG. 16B illustrates how the portion of first metatarsal 210 containing guide pin 650 has been rotationally realigned in the frontal plane. The angle of the guide pin 650 has rotated dorsally with rotation of the first metatarsal 210 and the sesamoid bones of have been centered plantarly under the metatarsal. In some examples, the first metatarsal 210 may translated in the transverse and/or sagittal plane in addition to being rotated in the frontal plane.

Figure 17B:
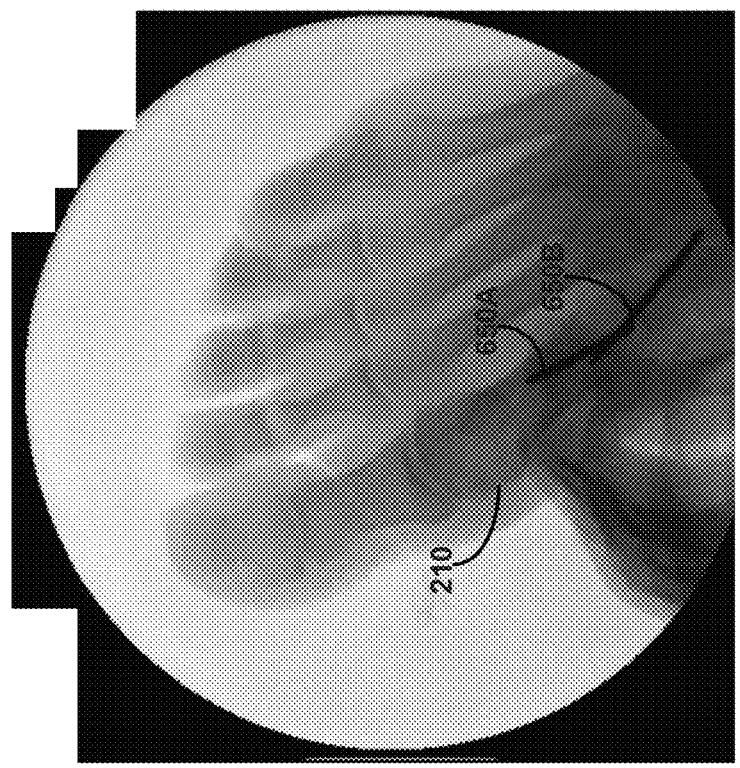
FIGS. 17A and 17B are additional example images showing how guide pins can be used during to help facilitate realignment of one bone portion relative to another bone portion.
Figure 17A:
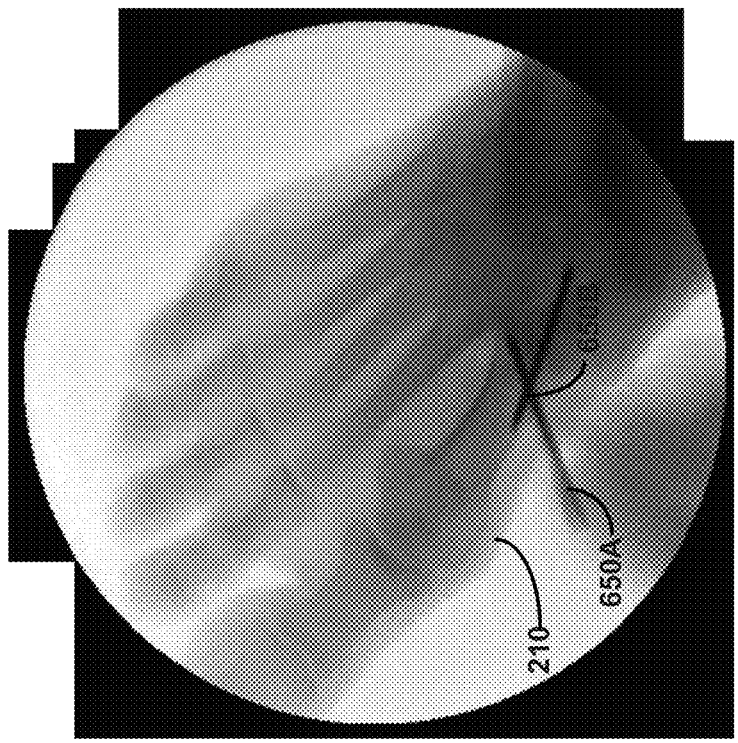

FIGS. 17A and 17B are additional example images showing how guide pins can be used to help facilitate realignment of one bone portion relative to another bone portion. FIG. 17A illustrates a first metatarsal 210 having frontal-plane rotation deviation. A first guide pin 650A is inserted into the metatarsal (e.g., in a distal portion of the metatarsal) while a second guide pin 650B is inserted proximally of the first guide pin (e.g., in a proximal portion of the metatarsal and/or medial cuneiform). The clinician can use the relative rotational positions of first and second guide pins 650A and 650B to help visually guide realignment of the distal portion of the first metatarsal (e.g., with the unaided eye and/or under fluoroscopic imaging). FIG. 17B illustrates how the portion of first metatarsal 210 containing first guide pin 650A has been rotationally realigned in the frontal plane relative to the second guide pin 650B. The angle of the first guide pin 650A has rotated dorsally into alignment with the second guide pin 650B. In some examples, the first metatarsal 210 may translated in the transverse and/or sagittal plane in addition to being rotated in the frontal plane.

Figure 18B:
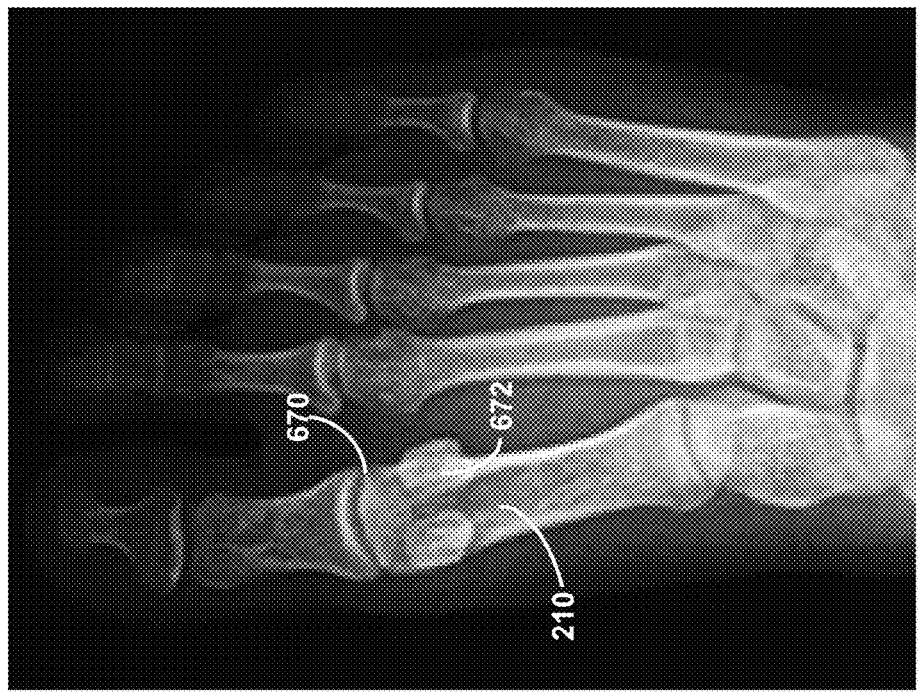
FIGS. 18A and 18B are fluoroscopic images showing example anatomical landmarks that a clinician may monitor to guide realignment of a bone portion.
Figure 18A:
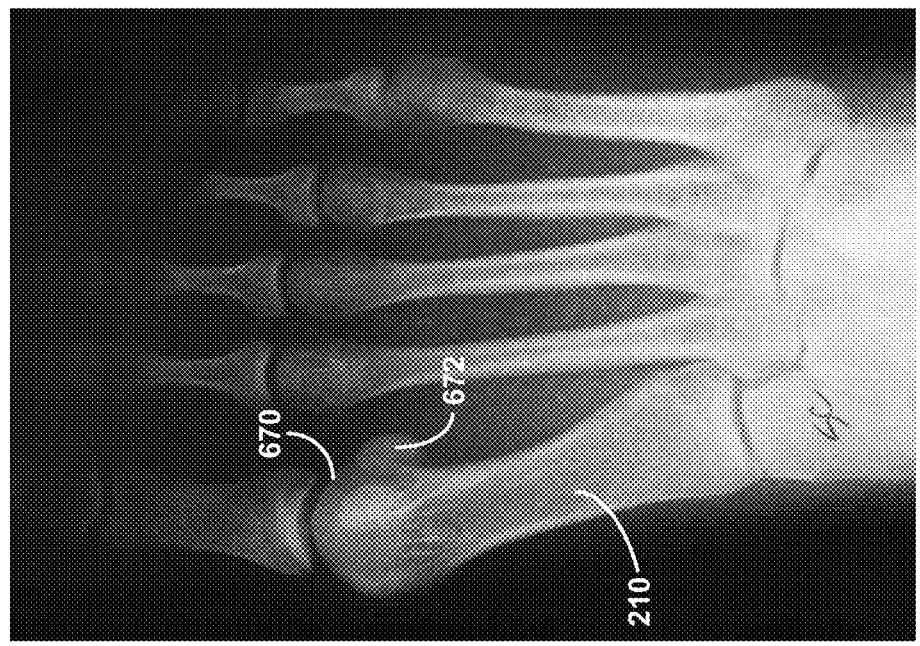

FIGS. 18A and 18B are fluoroscopic images showing example anatomical landmarks on a distal portion of a first metatarsal that a clinician may monitor (e.g., with the aid of fluoroscopy) to determine when the distal portion is suitably realigned relative to the proximal portion of the metatarsal. FIG. 18A is a fluoroscopic image taken from the dorsal-to-plantar direction showing a first metatarsal 210 that is misaligned in at least the frontal plane. In this example, the distal metatarsal head is characterized by a lateral rounding 670 in the transverse plane (the plane in the plane of the image), which is attributable to the frontal plane misalignment. As illustrated, the lateral rounding is the profile of the plantar condyles that come into view in the anterior-posterior projection with metatarsal frontal-plane rotation. Further, FIG. 18A illustrates that the sesamoid bones 672 are rotated laterally, also attributable to the frontal plane misalignment.

FIG. 18B is a fluoroscopic image taken from the dorsal-to-plantar direction showing the first metatarsal 210 from FIG. 18A that has been realigned in multiple planes. As shown, the lateral side 670 of the distal metatarsal head is substantially planar in the sagittal plane. In addition, the sesamoid bones 672 have rotated medially and are positioned substantially centered plantarly under the distal portion of the first metatarsal. Accordingly, FIGS. 18A and 18B illustrate that the profile of the metatarsal head and/or the position of the sesamoid bones are anatomical landmarks visible using fluoroscopy that a clinician can use to control realignment and determine when a distal bone portion is adequately realigned.

Various examples have been described. These and other examples are within the scope of the following claims.

The invention claimed is:

1. A method comprising:
   making a first crescentic-shaped cut transecting a first metatarsal, thereby forming a first metatarsal portion having a concave-shaped end and a second metatarsal portion having a convex-shaped end;
   making a second crescentic-shaped cut across the concave-shaped end of the first metatarsal portion or the convex-shaped end of the second metatarsal portion; and
   moving the second metatarsal portion in at least two planes relative to the first metatarsal portion, thereby adjusting an anatomical alignment of the second metatarsal portion.

2. The method of claim 1, wherein making the second crescentic-shaped cut comprises making the second crescentic-shaped cut across the concave-shaped end of the first metatarsal portion.

3. The method of claim 1, wherein making the first crescentic-shaped cut and making the second crescentic-shaped cut comprises making one of the first and second crescentic-shaped cuts parallel to a frontal plane, thereby forming the concave-shaped end in a transverse plane, and making the other of the first and second crescentic-shaped cuts at an acute angle to the transverse plane along an axis extending from a dorsal-medial side of the first metatarsal portion to a plantar-lateral side of the first metatarsal portion.

4. The method of claim 1, wherein making the first crescentic-shaped cut comprises making the first crescentic-shaped cut parallel to a frontal plane, thereby forming the concave-shaped end in a transverse plane.

5. The method of claim 1, wherein making the second crescentic-shaped cut comprises making the second crescentic-shaped along an axis extending from a dorsal-medial side of the first metatarsal portion to a plantar-lateral side of the first metatarsal portion.

6. The method of claim 1, wherein making the second crescentic-shaped cut comprises making the second crescentic-shaped cut at an acute angle to a transverse plane.

7. The method of claim 6, wherein the acute angle ranges from 10 degrees to 35 degrees.

8. The method of claim 1, wherein making the second crescentic-shaped cut across the concave-shaped end of the first metatarsal portion comprises making the second crescentic-shaped cut along a same frontal plane as that along which the first crescentic-shaped cut is made.

9. The method of claim 1, wherein the first metatarsal portion is a proximal portion of the first metatarsal and the second metatarsal portion is a distal portion of the first metatarsal.

10. The method of claim 1, wherein making the first crescentic-shaped cut comprises making the first crescentic-shaped cut on a proximal-most half of the first metatarsal.

11. The method of claim 10, wherein making the first crescentic-shaped cut comprises making the first crescentic-shaped cut on a proximal-most quarter of the first metatarsal.

12. The method of claim 1, wherein making the first crescentic-shaped cut comprises making the first crescentic-shaped cut with a generally crescent-shaped blade having a radius of curvature ranging from 3 millimeters to 15 millimeters.

13. The method of claim 12, wherein making the second crescentic-shaped cut comprises making the second crescentic-shaped cut with a generally crescent-shaped blade having a same radius of curvature as the generally crescent-shaped blade used to make the first crescentic-shaped cut.

14. The method of claim 1, wherein moving the second metatarsal portion in at least two planes relative to the first metatarsal portion comprises rotating the second metatarsal portion in a frontal plane.

15. The method of claim 14, wherein rotating the second metatarsal portion in the frontal plane comprises rotating the second metatarsal portion until a tibial sesamoid bone and a fibular sesamoid bone are on opposite sides of a sagittal plane when viewed from the frontal plane.

16. The method of claim 1, wherein moving the second metatarsal portion in at least two planes relative to the first metatarsal portion comprises pivoting the second metatarsal portion laterally in the transverse plane to reduce an intermetatarsal angle between the first metatarsal and a second metatarsal.

17. The method of claim 1, wherein moving the second metatarsal portion in at least two planes relative to the first metatarsal portion comprises moving the second metatarsal portion in frontal, transverse, and sagittal planes.

18. The method of claim 1, wherein
   forming the first metatarsal portion having the concave-shaped end comprises forming a first concavity;
   making the second crescentic-shaped cut comprises forming a second concavity intersecting the first concavity; and
   moving the second metatarsal portion relative to the first metatarsal portion comprises moving the convex-shaped end of the second metatarsal portion from the first concavity to the second concavity.

19. The method of claim 1, further comprising, subsequent to moving the second metatarsal portion relative to the first metatarsal portion, fixing the first metatarsal portion with respect to the second metatarsal portion.

20. The method of claim 19, wherein fixing the first metatarsal portion with respect to the second metatarsal portion comprises applying at least one of a bone plate, a pin, a screw, and a staple across a joint separating the first metatarsal portion from the second metatarsal portion.

21. The method of claim 20, wherein applying the bone plate comprises applying a bone plate selected from the group consisting of a helical-shaped bone plate, a T-shaped bone plate, and an L-shaped bone plate.

22. The method of claim 19, further comprising, prior to fixing the first metatarsal portion with respect to the second metatarsal portion, provisionally fixating a joint between the first metatarsal portion and the second metatarsal portion.

23. The method of claim 1, wherein
   moving the second metatarsal portion in at least two planes relative to the first metatarsal portion comprises visualizing the first metatarsal portion and the second metatarsal portion under fluoroscopy and monitoring a position of one or more anatomical landmarks visible under fluoroscopy to control adjustment of the anatomical alignment, the anatomical landmark comprising at least one of a plantar condyle and a sesamoid.

24. The method of claim 1, further comprising inserting a guide pin into at least the second metatarsal portion, wherein moving the second metatarsal portion comprises moving the second metatarsal portion via the guide pin.

25. A method comprising:

making a crescentic-shaped cut transecting a first metatarsal, thereby providing a first metatarsal portion having a concave-shaped end or a convex-shaped end and a second metatarsal portion having another of the concave-shaped end or the convex-shaped end;

making a planar cut across the first metatarsal at a location which, after making the crescentic-shaped cut, results in the second metatarsal portion having a planar end and an intermediate bone portion having a planar end on one side and the other of the concave-shaped end or the convex-shaped end on an opposite side; and moving the second metatarsal portion relative to the first metatarsal portion and the intermediate bone portion, thereby adjusting an anatomical alignment of the second metatarsal portion.

26. The method of claim 25, wherein the intermediate bone portion has the convex-shaped end.

27. The method of claim 25, wherein making the planar cut comprises making the planar cut prior to making the crescentic-shaped cut.

28. The method of claim 25, wherein the first metatarsal portion is a proximal portion and the second metatarsal portion is a distal portion.

29. The method of claim 25, wherein making the crescentic-shaped cut comprises making the crescentic-shaped cut parallel to a frontal plane, thereby forming the concave-shaped end in a transverse plane.

30. The method of claim 25, wherein
the second metatarsal portion has the convex-shaped end;
making the planar cut comprises making the planar cut after making the crescentic-shaped cut, the planar cut being offset from the convex-shaped end on the second metatarsal portion; and
the offset is a distance ranging from 2 to 30 millimeters from a terminal edge of the convex-shaped end.

31. The method of claim 25, wherein moving the second metatarsal portion relative to the first metatarsal portion and the intermediate bone portion comprises pivoting the second metatarsal portion and the intermediate portion laterally relative to the first metatarsal portion in a transverse plane and rotating the second metatarsal portion relative to the intermediate bone portion in a frontal plane.

32. The method of claim 31, wherein pivoting the second metatarsal portion and the intermediate bone portion laterally in the transverse plane comprises reducing an intermetatarsal angle between the first metatarsal portion and a second metatarsal.

33. The method of claim 31, wherein rotating the second metatarsal portion in the frontal plane comprises rotating the second metatarsal portion until a tibial sesamoid bone and a fibular sesamoid bone are on opposite sides of a sagittal plane when viewed from the frontal plane.

34. The method of claim 25, wherein moving the second metatarsal portion relative to the first metatarsal portion and the intermediate bone portion comprises moving the second metatarsal portion in frontal, transverse, and sagittal planes.

35. The method of claim 25, further comprising, subsequent to moving the second metatarsal portion relative to the first metatarsal portion, fixing the first metatarsal portion with respect to the second metatarsal portion.

36. The method of claim 35, wherein fixing the first metatarsal portion with respect to the second metatarsal portion comprises applying at least one of a bone plate, a pin, a screw, and a staple across a joint separating the first metatarsal portion from the second metatarsal portion.

* * * * *